(12) United States Patent
Kowata et al.

(10) Patent No.: US 11,553,864 B2
(45) Date of Patent: Jan. 17, 2023

(54) BIOLOGICAL SENSOR AND VEHICLE SEAT

(71) Applicant: TS TECH CO., LTD., Asaka (JP)

(72) Inventors: Kohei Kowata, Tochigi (JP); Tomoari Aiba, Tochigi (JP); Yoritaka Doi, Tochigi (JP)

(73) Assignee: TS TECH CO., LTD., Asaka (JP)

( * ) Notice: Subject to any disclaimer, the term of this patent is extended or adjusted under 35 U.S.C. 154(b) by 0 days.

(21) Appl. No.: 17/312,122

(22) PCT Filed: Dec. 11, 2019

(86) PCT No.: PCT/JP2019/048532
§ 371 (c)(1),
(2) Date: Jul. 29, 2021

(87) PCT Pub. No.: WO2020/122135
PCT Pub. Date: Jun. 18, 2020

(65) Prior Publication Data
US 2022/0039718 A1 Feb. 10, 2022

(30) Foreign Application Priority Data

Dec. 13, 2018 (JP) .............................. JP2018-233822
Dec. 13, 2018 (JP) .............................. JP2018-233826
(Continued)

(51) Int. Cl.
*G08B 23/00* (2006.01)
*A61B 5/18* (2006.01)
(Continued)

(52) U.S. Cl.
CPC .............. *A61B 5/18* (2013.01); *A61B 5/0245* (2013.01); *A61B 5/6893* (2013.01); *B60N 2/002* (2013.01); *B60N 2/64* (2013.01)

(58) Field of Classification Search
CPC ....... A61B 5/18; A61B 5/0245; A61B 5/6893; B60N 2/002; B60N 2/64
(Continued)

(56) References Cited

U.S. PATENT DOCUMENTS 5,234,738 A * 8/1993 Wolf ..................... E01C 13/045
428/44
6,220,667 B1 * 4/2001 Wagner .................. B60N 2/002
297/284.6
(Continued)

FOREIGN PATENT DOCUMENTS

JP 2004/148985 5/2004
JP 2006346093 12/2006
(Continued)

OTHER PUBLICATIONS

PCT International Preliminary Report on Patentability (w/ English translation) for corresponding PCT Application No. PCT/JP2019/048532, dated Jun. 8, 2021—12 pages.
(Continued)

*Primary Examiner* — Zhen Y Wu
(74) *Attorney, Agent, or Firm* — Dority & Manning, P.A.

(57) ABSTRACT

A biological sensor is provided with at least two sensors for detecting vibrations, and is configured so that the at least two sensors form layers. One of the at least two sensors is a first sensor used to acquire biological information, and one is a second sensor used to remove noise. A first cushion material for reducing vibrations is disposed between the first sensor and the second sensor. The first cushion material is integrally laminated with the first sensor and the second sensor. This facilitates accurate detection of biological information.

10 Claims, 22 Drawing Sheets

(30) Foreign Application Priority Data

Dec. 13, 2018 (JP) .............................. JP2018-233828
Dec. 13, 2018 (JP) .............................. JP2018-233829

(51) Int. Cl.
*A61B 5/0245* (2006.01)
*A61B 5/00* (2006.01)
*B60N 2/00* (2006.01)
*B60N 2/64* (2006.01)

(58) Field of Classification Search
USPC ........................................................ 340/576
See application file for complete search history.

(56) References Cited

U.S. PATENT DOCUMENTS

| | | | |
|---|---|---|---|
| 10,034,631 B1* | 7/2018 | Gallagher | B60N 2/0244 |
| 10,737,599 B2* | 8/2020 | Yoshikawa | B60N 2/2222 |
| 2002/0018576 A1* | 2/2002 | Shima | H04R 1/025 |
| | | | 381/396 |
| 2006/0155175 A1* | 7/2006 | Ogino | A61B 5/02438 |
| | | | 600/595 |
| 2006/0219459 A1* | 10/2006 | Suzuki | G08B 21/06 |
| | | | 340/425.5 |
| 2007/0049837 A1* | 3/2007 | Shertukde | A61B 7/00 |
| | | | 600/528 |
| 2012/0222486 A1* | 9/2012 | Lai | G01H 17/00 |
| | | | 73/649 |
| 2015/0229341 A1* | 8/2015 | Fung | G06K 9/0053 |
| | | | 702/191 |
| 2016/0003106 A1* | 1/2016 | Fouquet | C04B 37/005 |
| | | | 427/255.12 |
| 2016/0354027 A1* | 12/2016 | Benson | A61B 5/1102 |
| 2017/0313228 A1* | 11/2017 | Liu | A47C 7/28 |
| 2019/0035376 A1* | 1/2019 | Pilaar | G10K 11/168 |
| 2019/0063318 A1* | 2/2019 | Roach | G10K 11/168 |
| 2019/0106037 A1* | 4/2019 | Mankame | A47C 7/20 |
| 2019/0161157 A1* | 5/2019 | Ravise | G10K 11/172 |
| 2019/0248260 A1* | 8/2019 | Yoshikawa | B60N 2/2222 |
| 2020/0200699 A1* | 6/2020 | Kulkarni | G01N 27/4075 |
| 2022/0024352 A1* | 1/2022 | Kaku | A61B 5/6893 |

FOREIGN PATENT DOCUMENTS

| | | |
|---|---|---|
| JP | 2007290504 A | 11/2007 |
| JP | 2009262798 A | 11/2009 |
| JP | 2012243165 | 12/2012 |
| JP | 2013085896 | 5/2013 |
| JP | 2013205965 | 10/2013 |
| JP | 2016026516 | 2/2016 |
| JP | 2016/028659 | 3/2016 |
| JP | 2016/168177 | 9/2016 |
| JP | 2016210405 A | 12/2016 |
| JP | 2017171175 A | 9/2017 |
| JP | 2018045303 | 3/2018 |
| JP | 2018/097457 | 6/2018 |
| WO | WO 2005/023105 | 3/2005 |
| WO | WO 2006/057313 | 6/2006 |
| WO | WO2010/117061 A | 10/2010 |
| WO | WO2017/022677 A | 2/2017 |
| WO | WO2017/069235 A | 4/2017 |

OTHER PUBLICATIONS

PCT International Search Report (w/ English translation) for corresponding PCT Application No. PCT/JP2019/048532, dated Mar. 10, 2020, 5 pages.

Japanese Office Action (w/ English translation) for corresponding Japanese Application No. 2018-233822, dated Jun. 24, 2022, 8 pages.

Japanese Office Action (w/ English translation) for corresponding Japanese Application No. 2018-233828, dated Jun. 24, 2022, 6 pages.

Japanese Office Action (w/ English translation) for corresponding Japanese Application No. 2018-233829, drafting date Aug. 31, 2022, 8 pages.

Japanese Office Action (w/ English translation) for corresponding Japanese Application No. 2018-233826, dated Nov. 8, 2022, 13 pages.

* cited by examiner

|   | BLOOD PRESSURE CALCULATION EXPRESSION | CORRELATION COEFFICIENT | ERROR (mmHg) |
|---|---|---|---|
| A | −705 × PWTT + 235 | 0.55 | −8 to 8 |
| B | −670 × PWTT + 245 | 0.75 | −10 to 10 |
| C | −472 × PWTT + 188 | 0.63 | −10 to 10 |

BIOLOGICAL SENSOR AND VEHICLE SEAT

CROSS REFERENCE TO RELATED APPLICATIONS

This application is the U.S. national stage entry of International Application No. PCT/JP2019/048532 filed under the Patent Cooperation Treaty and having a filing date of Dec. 11, 2019, which claims priority to Japanese Patent Application No. 2018-233822 having a filing date of Dec. 13, 2018, Japanese Patent Application No. 2018-233826 having a filing date of Dec. 13, 2018, Japanese Patent Application No. 2018-233828 having a filing date of Dec. 13, 2018, and Japanese Patent Application No. 2018-233829 having a filing date of Dec. 13, 2018, all of which are incorporated herein by reference.

TECHNICAL FIELD

The present invention relates to a biological sensor and a vehicle seat.

BACKGROUND ART

Deterioration of health condition of a driver who drives a vehicle can adversely affect driving of the vehicle. It is desirable to detect deterioration of health condition in advance and take some measures. As such a measure, known technique recognizes health condition of the driver. A non-contact blood flow sensor embedded in a seat and a backrest for the seat measures pulse waves and the like. Biological information such as a blood flow and a blood pressure are estimated based on measurement results (see Patent Document 1).

CITATION LIST

Patent Literature

Patent Literature 1: JP 2016-168177 A

SUMMARY OF INVENTION

Technical Problem

In a case where a vehicle is equipped with a biological sensor that detects biological information, vibration from the vehicle and minute vibration on a body surface of a living body are likely to cause noise. Therefore, it is necessary to remove noise as needed. However, it is difficult to remove noise by using only one biological sensor, and sometimes it is difficult to accurately detect biological information.

The present invention has been made in view of the above circumstances. An object of the present invention is to provide a biological sensor and a vehicle seat that facilitates accurate detection of biological information.

Solution to Problem

To achieve the above object, the invention according to claim 1 is a biological sensor, including:
  at least two sensors which detect vibration and which are layered,
  wherein, of the at least two sensors, one is a first sensor used to acquire biological information, and another is a second sensor used to remove noise.

The invention according to claim 2 is the biological sensor according to claim 1, further including:
  a first cushion material which is placed between the first sensor and the second sensor and which attenuates vibration,
  wherein the first cushion material is layered with the first sensor and the second sensor.

The invention according to claim 3 is the biological sensor according to claim 2, wherein the first cushion material is made of a urethane slab.

The invention according to claim 4 is the biological sensor according to claim 2, wherein the first cushion material is constituted by cones.

The invention according to claim 5 is the biological sensor according to any one of claims 1 to 4, further including:
  a third sensor which is used to remove noise,
  wherein the third sensor is layered with the first sensor and the second sensor, and is on a side of the second sensor which does not face the first sensor.

The invention according to claim 6 is the biological sensor according to any one of claims 2 to 4, further including:
  a second cushion material that attenuates vibration,
  wherein the second cushion material is layered with the first sensor, the second sensor, and the first cushion material, and is on a side of the second sensor which does not face the first sensor.

The invention according to claim 7 is the biological sensor according to any one of claims 1 to 6, wherein the first sensor and the second sensor have the same shapes and the same sizes.

The invention according to claim 8 is the biological sensor according to any one of claims 1 to 6, wherein one of the first sensor and the second sensor is larger than another.

The invention according to claim 9 is a vehicle seat, including:
  the biological sensor according to any one of claims 1 to 8,
  wherein the first sensor is placed on a side closer to a living body, and the second sensor is placed on a side farther from the living body.

The invention according to claim 10 is the vehicle seat according to claim 9, further including:
  a first cushion material which attenuates vibration and which is placed between the first sensor and the second sensor so as to be layered with the first sensor and the second sensor; and
  a calculation unit that calculates to perform calibration by amplifying the vibration by an amount attenuated by the first cushion material.

Advantageous Effects of Invention

According to the invention of claim 1, the first sensor and the second sensor that detect vibration are layered. The same noise which is not biological information is included in each of signals detected by the first sensor and the second sensor. A difference between noise components is taken from biological information including a noise component which is acquired by the first sensor. Thereby, only biological information is extracted. Further, an error in detection of the noise components is unlikely to occur between the first sensor and the second sensor being layered. Accurate detection of biological information is facilitated.

According to the invention of claim 2, vibration transmitted from the first sensor to the second sensor is attenuated by the first cushion material. Therefore, biological information is easily extracted.

The first cushion material prevents contact between the first sensor and the second sensor. Therefore, the first sensor and the second sensor are less likely to be damaged.

According to the invention of claim 3, since the first cushion material is made of a urethane slab, it is easy to be processed. It is easy to layer the first cushion material with the first sensor and the second sensor.

According to the invention of claim 4, the first cushion material is constituted by cones. Therefore, it is difficult for vibration generated on a tip of the cone to be transmitted to a bottom of the cone. It increases an attenuation rate in attenuation of vibration by the first cushioning material.

According to the invention of claim 5, when the difference between the noise components is taken from the biological information including the noise component acquired by the first sensor, the difference is taken in two steps. It improves accuracy of extracted biological information.

According to the invention of claim 6, the second cushion material attenuates vibration from the second sensor side. It improves accuracy of extracted biological information.

According to the invention of claim 7, the first sensor and the second sensor have the same shape and the same size. Therefore, the first sensor and the second sensor have the same range of detection of vibration.

When a product in which the first sensor and the second sensor being layered is manufactured, the biological sensor is easily formed in a good shape.

According to the invention of claim 8, one of the first sensor and the second sensor is larger than the other. Therefore, the range of vibration of detection by one sensor is wider.

According to the invention of claim 9, the first sensor is arranged on a side closer to a living body, and the second sensor is arranged on a side farther from the living body. Therefore, the first sensor can easily acquire biological information.

According to the invention of claim 10, the calculation unit calculates to perform calibration by amplifying vibration by an amount attenuated by the first cushion material. Therefore, biological information from which a noise component has been removed is acquired.

BRIEF DESCRIPTION OF DRAWINGS

FIG. 11 shows a vehicle seat provided with a lumbar support, a bank, a height mechanism, and the like.

DESCRIPTION OF EMBODIMENTS

Hereinafter, embodiments of the present invention will be described with reference to the drawings. The embodiments described below have various technically preferable limitations for carrying out the present invention. However, the technical scope of the present invention is not limited to the following embodiments and illustrated examples.

First Embodiment

Figure 1:
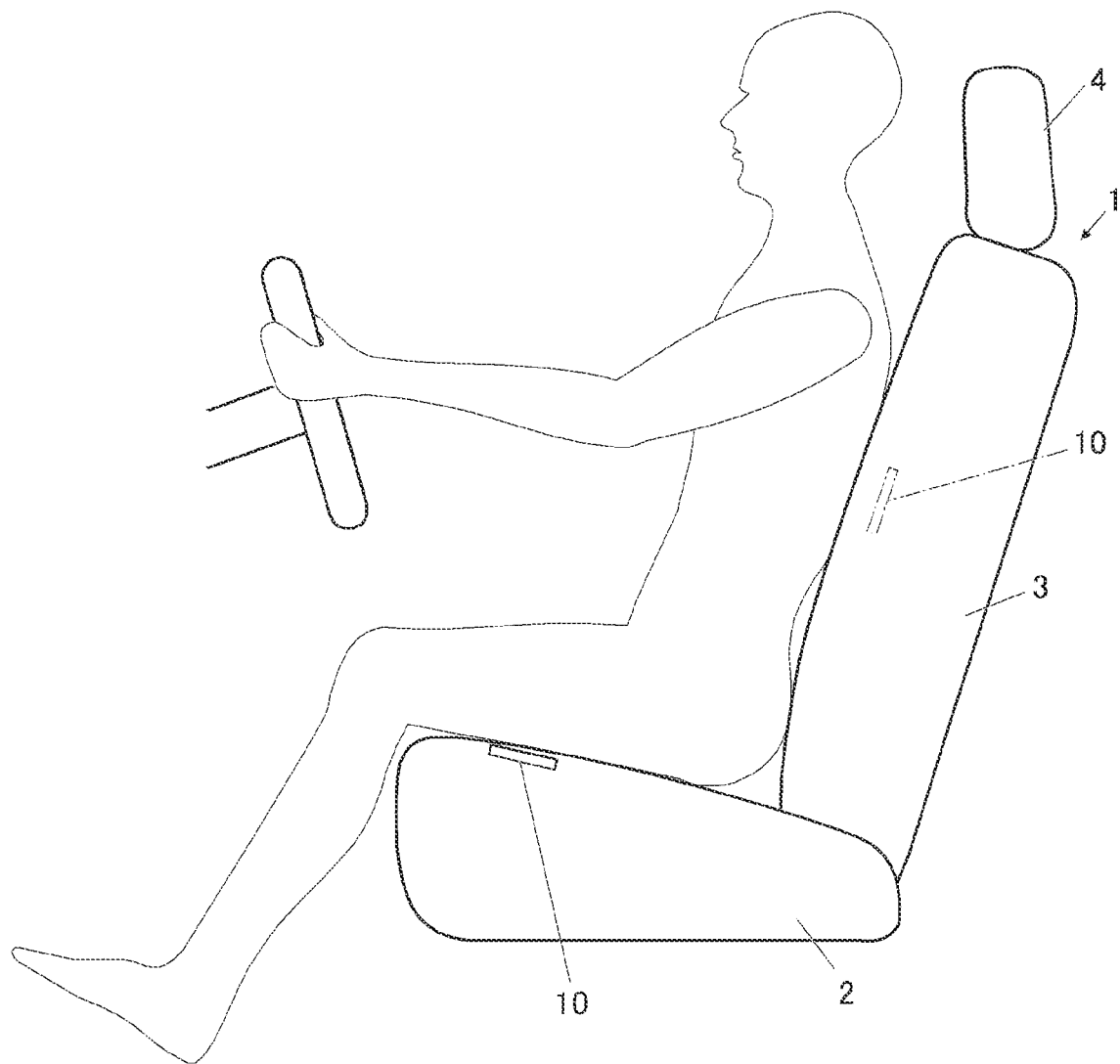
FIG. 1 is a side view showing a vehicle seat provided with a biological sensor.

In FIG. 1, the reference numeral 1 indicates a vehicle seat (hereinafter referred to as "seat 1") on which a person sits. The seat 1 is provided in a vehicle such as an automobile. The vehicle may travel while being driven only manually. Alternatively, the vehicle may travel while switching between automatic driving and manual driving.

The seat 1 includes:
a seat cushion 2 that supports buttocks and thighs of a person;
a seat back 3 which serves as a backrest and which has a lower end supported by the seat cushion 2; and
a headrest 4 provided on the seat back 3 to support a head of a person.
The seat cushion 2 mainly includes:
a seat cushion frame that is a skeleton;
a cushion pad provided on the seat cushion frame; and
a cover that covers the seat cushion frame and the cushion pad.
The seat back 3 mainly includes:
a seat back frame that is a skeleton;
a cushion pad provided on the seat back frame; and
a cover that covers the seat back frame and the cushion pad.

A biological sensor 10 as a means for recognizing health condition of a seated person (living body) is provided in the seat 1. More specifically, the biological sensor 10 in the embodiment detects pulse waves as biological information from a blood flow at a position opposite to a skin surface of a seated person.

It is desirable that the biological sensor 10 is provided at a position closer to a seated person. In the embodiment, the biological sensor 10 is provided at a front end of the seat cushion 2 on an upper side of the cushion pad and on an inner side of the cover. The biological sensor 10 is located on a lower side of a thigh of the seated person.

The biological sensor 10 in the embodiment is provided in the seat cushion 2. Alternatively, as shown in FIG. 1, the biological sensor 10 may be provided in the seat back 3. Also in this case, the biological sensor 10 is provided on the cushion pad of the seat back 3 on a side of a seated person and on an inner side of the cover.

Figure 2:
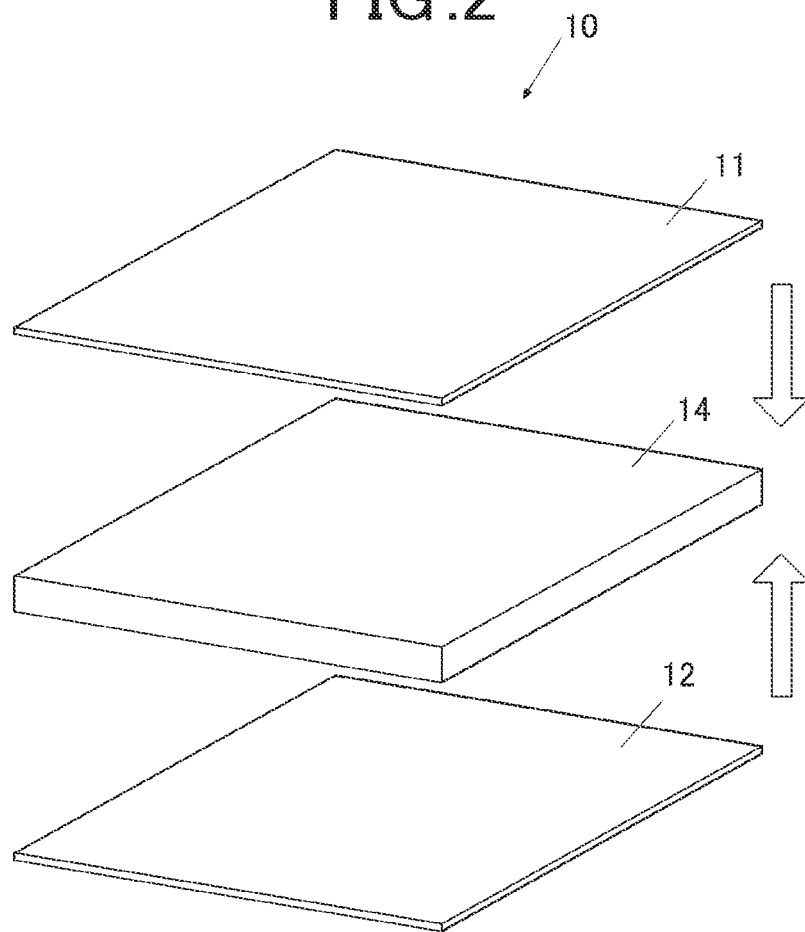
FIG. 2 is a perspective view showing a structure of the biological sensor.

A structure of the biological sensor 10 in the embodiment will be described in more detail. As shown in FIG. 2, the biological sensor 10 includes at least two sensors 11, 12 that detect vibration. These at least two sensors 11, 12 are layered. Of the at least two sensors 11, 12, one is a first sensor 11 used to acquire biological information. The other is a second sensor 12 used to remove noise.

A first cushion material 14 for attenuating vibration is arranged between the first sensor 11 and the second sensor 12. The first cushion material 14 is layered with the first sensor 11 and the second sensor 12.

That is, in the biological sensor 10, the first sensor 11, the second sensor 12, and the first cushion material 14 are layered. The first cushion material 14 is sandwiched between the first sensor 11 and the second sensor 12.

In the three-layer structure of the embodiment, the first sensor 11, the first cushion material 14, and the second sensor 12 are layered in this order. The biological sensor 10 is not limited to this. The biological sensor 10 may have a two-layer structure of the first sensor 11 and the second sensor 12 as long as vibration transmitted between the first sensor 11 and the second sensor 12 can be attenuated.

The same sensors are used for the first sensor 11 and the second sensor 12. As the first sensor 11 and the second sensor 12 in the embodiment, a piezoelectric sensor that detects pressure waves on a body surface of a seated person is used.

The piezoelectric sensor detects the pressure waves on the body surface of the seated person by a piezoelectric element. The piezoelectric sensor is a contact type sensor that touches the seated person. The piezoelectric sensor is not limited to this. A non-contact sensor that does not need to contact a seated person may be used.

As the first sensor 11 and the second sensor 12, for example, a photoelectric sensor, an electromagnetic wave sensor, an acceleration sensor to which a MEMS (micro electro mechanical system) is applied, or the like can be used in addition to the piezoelectric sensor.

The photoelectric sensor is a non-contact type sensor. The photoelectric sensor irradiates a seated body with light from a light emitter. A light receiver of the photoelectric sensor receives the reflected light. The photoelectric sensor detects pulse waves from the reflected light. The electromagnetic wave sensor is a non-contact type sensor. The electromagnetic wave sensor irradiates a seated body with electromagnetic waves. The electromagnetic wave sensor detects pulse waves from reflected waves from the seated body.

The acceleration sensor to which the MEMS is applied is a contact type sensor. As a detection element, a MEMS including, for example, a fine weight is used for the acceleration sensor. The acceleration sensor detects pulse waves from displacement of the weight.

The first sensor 11 and the second sensor 12 have the same shapes and the same sizes.

The first cushion material 14 is made of a urethane slab and has the same shape as the first sensor 11 and the second sensor 12. The first cushion material 14 is thicker than the first sensor 11 and the second sensor 12. Although the first cushion material 14 in the embodiment is made of a urethane slab, the first cushion material 14 is not limited to this. For example, the first cushion material 14 may be made of damping rubber.

In a case where the biological sensor 10 is provided in the seat 1, the first sensor 11 used for acquiring biological information is placed on a side closer to a seated person. The second sensor 12 used for removing noise is placed on a side farther from the seated person.

Figure 3:
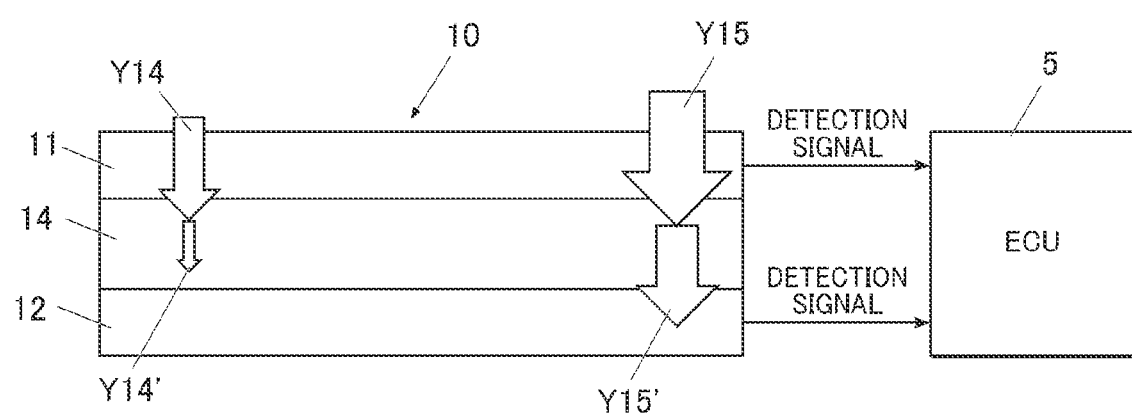
FIG. 3 illustrates an outline of system configuration for acquiring biological information.

As shown in FIG. 3, a calculation unit is provided in the seat 1 or somewhere in a vehicle. The calculation unit is connected to each of the first sensor 11 and the second sensor 12 so as to be capable of data communication. The calculation unit in the embodiment is constituted by a control device 5 provided on the seat 1. The control device 5 is also called a so-called ECU (electronic controller).

Thus, the control device 5 and the biological sensor 10 provided with the first sensor 11 and the second sensor 12 are connected so as to be capable of data communication. Thereby, a system for acquiring biological information is constructed.

Two types of vibration are transmitted to the biological sensor 10 to acquire biological information of a person sitting on the seat 1.

The two types of vibration are:
vibration with a small amplitude due to pulse waves (arrow Y14 in FIG. 3); and
load change vibration with a large amplitude due to vehicle vibration (arrow Y15 in FIG. 3).

The first sensor 11 arranged on the side closer to a seated person detects two types of vibration (arrows Y14, Y15) that are not attenuated by the first cushion material 14. On the other hand, the second sensor 12 arranged on the side farther from the seated person across the first cushion material 14 sometimes does not detect the vibration with a small amplitude due to pulse waves between the two types of vibration. The arrow Y14' in FIG. 3 indicates vibration caused by an attenuated pulse wave. The second sensor 12 detects at least load change vibration (arrow Y15' in FIG. 3).

Thus, the biological sensor 10 is configured such that the first sensor 11 and the second sensor 12 are layered. Thereby, vibration of the same type, that is, load change vibration Y15, Y15' with a large amplitude due to vehicle vibration, enters the first sensor 11 and the second sensor 12. The vibration Y14 (Y14') with the small amplitude due to pulse waves can be detected by the first sensor 11, but is unlikely to be transmitted to the second sensor 12.

The control device 5 which is a calculation unit includes memory in which a calculation program is stored. The control device 5 uses detection signals (data) detected by the first sensor 11 and the second sensor 12. The control device 5 derives pulse waves by an arithmetic program. At this time, the control device 5 calculates by performing calibration so as to amplify vibration by an amount attenuated by the first cushion material 14.

A detection signal detected by the first sensor 11 and transmitted to the control device 5 includes not only pulse waves to be extracted but also a noise component.

To remove the noise component, the control device 5 performs calculation so as to take a difference between:

the detection signal detected by the first sensor 11 and transmitted to the control device 5; and a detection signal detected by the second sensor 12 and transmitted to the control device 5.

However, as described above, the vibration due to pulse waves is unlikely to be transmitted to the second sensor 12. Sometimes pulse waves cannot be accurately obtained only by taking the difference. Therefore, at the time of calculation, calibration is performed by amplifying vibration by an amount attenuated by the first cushion material 14. Thereby, only the noise component is removed, and only a detection signal of pulse waves (biological information) is extracted.

In a case where the biological sensor 10 has a two-layer structure including the first sensor 11 and the second sensor 12 which do not include the first cushion material 14, the vibration Y14 (Y14') with the small amplitude due to pulse waves is easily transmitted to the second sensor 12, too. In such a case, it is not necessary to perform calibration by amplifying the vibration by an amount attenuated by the first cushion material 14.

The detection signal of the extracted pulse wave is used, for example, to estimate a blood pressure of a seated person. To estimate a blood pressure from pulse waves, for example, another biological sensor 10 is provided at another position of the seat 1. A blood pressure is derived from pulse wave transit speed. Alternatively, a blood pressure may be derived by other blood pressure estimation methods that meet the IEEE standard (IEEE 1708-2014).

According to the embodiment, the first sensor 11 and the second sensor 12 that detect vibration are layered. The same noise which is not biological information is included in each of signals detected by the first sensor 11 and the second sensor 12. Therefore, a difference between noise components is obtained from biological information including a noise component acquired by the first sensor 11. Only biological information is extracted. An error in detecting a noise component is unlikely to occur between the first sensor 11 and the second sensor 12 being layered. Accurate detection of biological information is facilitated.

The first cushion material 14 attenuates vibration transmitted from the first sensor 11 to the second sensor 12. Therefore, biological information is easily extracted.

Further, the first cushion material 14 prevents contact between the first sensor 11 and the second sensor 12. Therefore, the first sensor 11 and the second sensor 12 are less likely to be damaged.

The first cushion material 14 is made of a urethane slab and can easily be processed. The first cushion material 14 can easily be layered with the first sensor 11 and the second sensor 12.

The first sensor 11 and the second sensor 12 have the same shapes and the same sizes. Therefore, ranges of detection of vibration by the first sensor 11 and the second sensor 12 are the same.

When a product in which the first sensor 11 and the second sensor 12 being layered is manufactured, the biological sensor 10 is easily formed in a good shape.

The first sensor 11 is placed on a side closer to a seated person, and the second sensor 12 is placed on a side farther from the seated person. Therefore, the first sensor 11 can easily acquire biological information.

The control device 5 which is the calculation unit calculates to perform calibration by amplifying vibration by an amount attenuated by the first cushion material. Therefore, biological information from which a noise component has been removed is acquired.

Modification

Embodiments to which the present invention can be applied is not limited to the above embodiment. Embodiments can be modified within the scope of the claims of the present invention. Modifications will be described below. The following modifications may be combined in possible ways. Common reference numerals are given to elements common to the above embodiment and the following modifications. Explanation is omitted or simplified.

Modification 1

Figure 4:
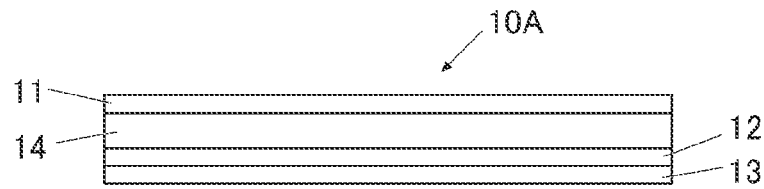
FIG. 4 is a side view showing a modification of the biological sensor.

As shown in FIG. 4, the biological sensor 10A in the modification includes the third sensor 13 on a side of the second sensor 12 which does not face the first sensor 11. The third sensor 13 forms a four-layer structure by being layered with the first sensor 11 and the second sensor 12. The third sensor 13 is used to remove noise.

That is, sensors are layered such that:

the first cushion material 14 is provided between the first sensor 11 and the second sensor 12; and the second sensor 12 is provided between the first cushion material 14 and the third sensor 13.

As the third sensor 13, the same type of sensor as the first sensor 11 and the second sensor 12 is used. The third sensor 13 is also connected to the control device 5 which is the calculation unit so that data communication is possible.

According to the modification, to take a difference between noise components from biological information including a noise component which is acquired by the first sensor 11, the difference is taken in two steps using the second sensor 12 and the third sensor 13. It improves accuracy of extracted biological information.

Modification 2

Figure 5:
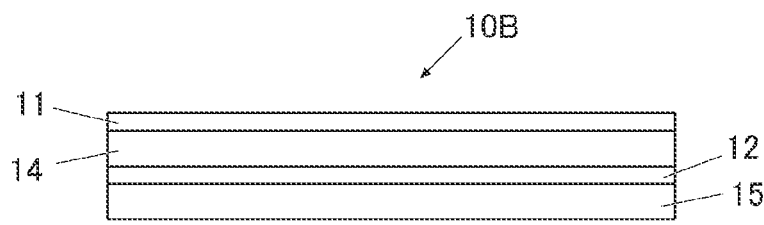
FIG. 5 is a side view showing a modification of the biological sensor.

As shown in FIG. 5, the biological sensor 10B in the modification includes the second cushion material 15 on a side of the second sensor 12 which does not face the first sensor 11. The second cushion material 15 forms a four-layer structure by being layered with the first sensor 11, the second sensor 12, and the first cushion material 14. The second cushion material 15 attenuates vibration.

That is, sensors are layered such that:

the first cushion material 14 is provided between the first sensor 11 and the second sensor 12; and the second sensor 12 is provided between the first cushion material 14 and the second cushion material 15.

The second cushion material 15 is made of a urethane slab like the first cushion material 14. The material is not limited to this. The second cushion material 15 may be made of other materials such as damping rubber.

The first cushion material 14 and the second cushion material 15 have the same shapes and the same sizes.

According to the modification, the second cushion material 15 attenuates vibration from the second sensor 12 side, that is, the side farther from a seated person, for example, a floor side of a vehicle. It improves accuracy of extracted biological information.

Modification 3

Figure 6A:
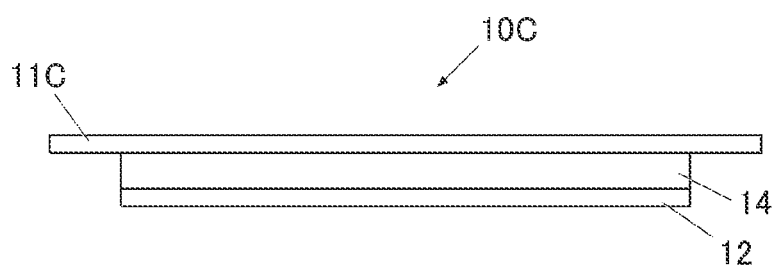
FIG. 6A is a side view showing a modification of the biological sensor.
Figure 6B:
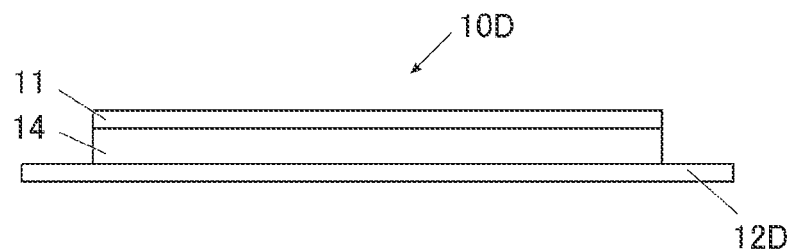
FIG. 6B is a side view showing a modification of the biological sensor.

As shown in FIGS. 6A and 6B, according to biological sensors 10C, 10D in the modification, one of the first sensor 11 (11C) and the second sensor 12 (12D) is larger than the other.

In an example shown in FIG. 6A, the first sensor 11C is larger than the second sensor 12.

In an example shown in FIG. 6B, the second sensor 12D is larger than the first sensor 11.

The first cushion material 14 has a size that fits the smaller sensor in both the examples shown in FIGS. 6A to 6B. Alternatively, the first cushion material 14 may have a size that fits the larger sensor. The first cushion material 14 may have a substantially trapezium shape that gradually spreads from a side of the smaller sensor to a side of the larger sensor.

According to the modification, one of the first sensor 11 (11C) and the second sensor 12 (12D) is larger than the other. It widens a detection range of vibration by one sensor.

Modification 4

Figure 7:
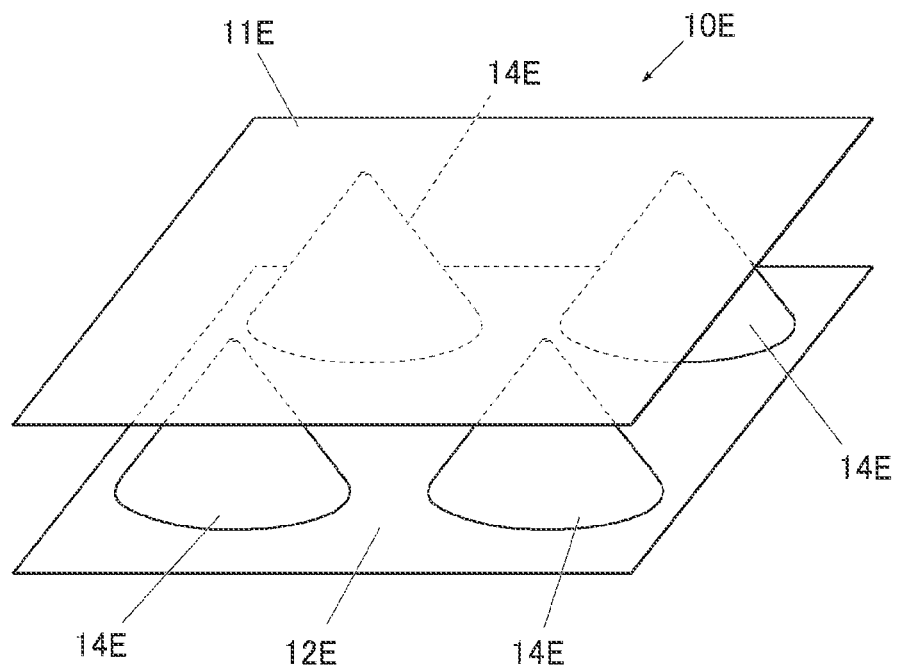
FIG. 7 is a side view showing a modification of the biological sensor.

As shown in FIG. 7, the biological sensor 10E in the modification includes a first cushion material constituted by cones 14E.

The first sensor 11E and the second sensor 12E are constituted by sensors each formed in a film shape. Alternatively, the first sensor 11E and the second sensor 12E may be constituted by sensors 11, 12 not formed in film shapes, similar to the above-described embodiment.

Each of the cones 14E has a property of a cone shape in which vibration generated on a tip is unlikely to be transmitted to a bottom. Therefore, these cones 14E do not have to be as soft as urethane foam, for example. The cones 14E may be made of a material that is hard enough not to impair seating comfort of a seated person.

According to the modification, the first cushion material is constituted by the cones 14E. Therefore, vibration generated on the tip of the cone 14E is difficult to be transmitted to the bottom of the cone 14E. It increases an attenuation rate in attenuation of vibration by the first cushioning material.

Modification 5

In the above embodiment and modifications, two types of vibration are transmitted to the biological sensor 10.

The two types of vibration are:
vibration with a small amplitude due to pulse waves; and
load change vibration with a large amplitude due to vehicle vibration.

The biological sensor 10 acquires pulse waves of a seated person based on them. In the modification, biological information other than pulse waves is acquired.

Biological information other than pulse waves is one that is acquired based on vibration detected by a sensor, such as heartbeats, respiration, or muscle contraction.

According to the modification, biological information of various kinds is acquired in addition to pulse waves by applying the layered structures of the first sensor 11 and the second sensor 12 in the embodiment and the modifications.

Second Embodiment

Next, a second embodiment of the present invention will be described with reference to the drawings. For convenience of explanation, the same reference numerals are given to components common to the first and second embodiments. Components different from the first embodiment will be mainly described. Duplicate explanations are given when necessary.

Biological information is sometimes difficult to be detected accurately, depending on positional relation between:
a seat provided with a sensor that detects biological information; and
a part of a body of a person sitting on the seat.

The second problem is to make it easier to detect biological information accurately.

To solve such a problem, the eleventh invention shown in an embodiment is a vehicle seat, including:
a seat body on which a person sits;
a biological sensor provided on a part of the seat body, the part being able to be moved to adjust a relative position with respect to a body of the seated person; and
a controller that controls movement of the part of the seat body.

The twelfth invention shown in the embodiment is the vehicle seat according to the eleventh invention, wherein, in a case where the controller determines that the biological sensor cannot acquire biological information to be acquired, the controller controls movement of the part of the seat body.

The thirteenth invention shown in the embodiment is the vehicle seat according to the eleventh or twelfth invention, wherein
the controller presses the biological sensor against the seated person by operating the part,
in a case where an output of the biological sensor pressed against the seated person exceeds a first threshold value, the controller makes the part move in a direction in which the biological sensor is separated from the seated person,
in a case where an output of the biological sensor moving away is below a second threshold value, the controller makes the part move in a direction in which the biological sensor approaches the seated person, and
in a case where an output of the biological sensor approaching and contacting the seated person exceeds a third threshold value, the controller stops movement of the part.

The fourteenth invention shown in the embodiment is the vehicle seat according to any one of the eleventh to thirteenth inventions, wherein
the seat body includes a seat cushion that supports buttocks and thighs of the seated person,
the seat cushion includes a cushion tilt mechanism which raises and lowers a front end of the seat cushion with respect to a rear end, and
the part is the front end of the seat cushion.

The fifteenth invention shown in the embodiment is the vehicle seat according to any one of the eleventh to fourteenth inventions, wherein
the seat body includes a seat back that supports a back and a waist of the seated person,
the seat back includes a lumbar support which is built into the seat back and which deforms in back and forth directions, and
the part is the lumbar support.

The sixteenth invention shown in the embodiment is the vehicle seat according to any one of the eleventh to fifteenth inventions, wherein the seat body includes a bag which is built into the seat body and which is inflated by being filled with fluid, and the part is a part of the bag of the seat body which is on a side of the seated person.

The seventeenth invention shown in the embodiment is the vehicle seat according to any one of the eleventh to sixteenth inventions, wherein the seat body includes a bank which is provided on an outer edge of the seat body and which moves in directions toward and away from the seated person, and the part is the bank.

The eighteenth invention shown in the embodiment is the vehicle seat according to any one of the eleventh to seventeenth inventions, wherein the seat body includes a seat cushion that supports buttocks and thighs of the seated person, the seat cushion includes a cushion front-rear length adjustment mechanism which adjusts a length in the back and forth directions by moving the front end of the seat cushion in the back and forth directions with respect to the rear end, and the part is the front end of the seat cushion.

The nineteenth invention shown in the embodiment is the vehicle seat according to any one of the eleventh to eighteenth inventions, wherein the seat body includes a seat cushion that supports buttocks and thighs of the seated person, the seat cushion includes a height mechanism that raises and lowers the seat cushion, and the part is the front end of the seat cushion.

The twentieth invention shown in the embodiment is the vehicle seat according to any one of the eleventh to nineteenth inventions, wherein the seat body includes:

a seat cushion that supports buttocks and thighs of the seated person;

a seat back that supports a back and a waist of the seated person; and a build detection sensor which detects a build of the seated person and which sends build detection information to the controller, and the build detection sensor includes:

a transmitter which is provided in the seat cushion and which irradiates the seat back with electromagnetic waves in a scanning line; and receivers which are provided in a grid pattern in the seat back and which receive the electromagnetic waves emitted from the transmitter.

According to the eleventh invention, the controller controls movement of the part, which can be moved to adjust a relative position with respect to a body of a seated person. Positional relation between the biological sensor provided at the part and a seated person is optimized. Accurate detection of biological information is facilitated.

According to the twelfth invention, the part of the seat body can be moved such that the biological sensor can acquire biological information to be acquired. Accurate detection of biological information is facilitated.

On the contrary, in a case where it is determined that the biological sensor can acquire biological information to be acquired, the controller can prevent the part of the seat body from moving. It eliminates unnecessary movement of the part.

According to the thirteenth invention, the controller controls movement of the part of the seat body so as to meet conditions of the first to third threshold values. Thereby, the controller determines whether the optimum positional relation between the biological sensor and a seated person is achieved.

The positional relation concerns, for example:

whether the biological sensor is in too strong contact with a seated person;

whether the biological sensor is separated from a seated person; and whether the biological sensor is in proper contact with a seated person.

According to the fourteenth invention, the part of the seat body is the front end of the seat cushion which is raised and lowered by the cushion tilt mechanism. The controller can control the front end of the seat cushion to make the biological sensor touch and leave a seated person.

According to the fifteenth invention, the part of the seat body is the lumbar support that deforms in the back and forth directions. The controller controls the lumbar support to make the biological sensor touch and leave a seated person.

In a case where the seat back includes a reclining mechanism, biological information of a seated person can be acquired also in a reclining state.

According to the sixteenth invention, the part of the seat body is a part of the bag of the seat body on a side of a seated person. The controller controls the bag to bulge and shrink. Thereby, the controller makes the biological sensor touch and leave a seated person.

According to the seventeenth invention, the part of the seat body is the bank that moves in the directions toward and away from the seated person. The controller controls the bank to make the biological sensor touch and leave a seated person.

According to the eighteenth invention, the part of the seat body is the front end of the seat cushion. The front end of the seat cushion is moved in the back and forth directions with respect to the rear end by the cushion front-rear length adjustment mechanism. The controller can control the front end of the seat cushion to make the biological sensor touch and leave a seated person.

According to the nineteenth invention, the part of the seat body is the front end of the seat cushion. The front end of the seat cushion is raised and lowered by the height mechanism. The controller can control the front end of the seat cushion to make the biological sensor touch and leave a seated person.

According to the twentieth invention, the build detection sensor includes:

a transmitter that irradiates the seat back with electromagnetic waves in a scanning line; and receivers provided in a grid pattern in the seat back.

Therefore, a build of an upper body of a seated person can be detected. The controller can control movement of the part provided with the biological sensor based on the build detection information. More accurate detection of biological information is facilitated.

Embodiments will be further described. The reference numeral 1 in FIG. 8 indicates a vehicle seat (hereinafter referred to as seat 1) on which a person sits. The seat 1 is provided in a vehicle such as an automobile. The vehicle may travel while being driven only manually. Alternatively, the vehicle may travel while switching between automatic driving and manual driving.

The seat 1 includes a seat body on which a person (hereinafter referred to as a seated person) is sits.

The seat body includes:

a seat cushion 2 that supports buttocks and thighs of a person; and a seat back 3 which includes a lower end supported by the seat cushion 2 to serve as a backrest, and which supports a back and a waist of the seated person.

A headrest that supports a head of a person is provided at an upper end of the seat back 3 of the seat body.

The seat cushion 2 mainly includes:

a seat cushion frame that is a skeleton;

a cushion pad provided on the seat cushion frame; and a cover that covers the seat cushion frame and the cushion pad.

The seat back 3 mainly includes:

a seat back frame that is a skeleton;

a cushion pad provided on the seat back frame; and a cover that covers the seat back frame and the cushion pad.

The seat 1 is provided with the biological sensor 10 as a means for recognizing health condition of a seated person (living body). More specifically, the biological sensor 10 in the embodiment detects pulse waves as biological information from a blood flow at a position opposite to a skin surface of a seated person.

It is desirable that the biological sensor 10 is provided at a position closer to a seated person. In the embodiment, the biological sensor 10 is provided at a front end of the seat cushion 2 on an upper side of the cushion pad and on an inner side of the cover. The biological sensor 10 is placed on a lower side of a thigh of the seated person.

Although the biological sensor 10 in the embodiment is provided in the seat cushion 2, the biological sensor 10 may be provided in the seat back 3. Also in that case, the biological sensor 10 is provided on the cushion pad of the seat back 3 on a side of a seated person and on an inner side of the cover.

The biological sensor 10 in the embodiment is a piezoelectric sensor that detects pressure waves on a body surface of a seated person.

The piezoelectric sensor detects the pressure waves on the body surface of the seated person by a piezoelectric element. The piezoelectric sensor is a contact type sensor that touches the seated person.

In the embodiment, the piezoelectric sensor is used as the biological sensor 10. The biological sensor 10 is not limited to this. The biological sensor 10 can be modified as long as the sensor can approach and touch a seated person to acquire biological information. Conversely, a sensor that cannot acquire biological information unless it is separated from a seated person is not used.

Figure 8:
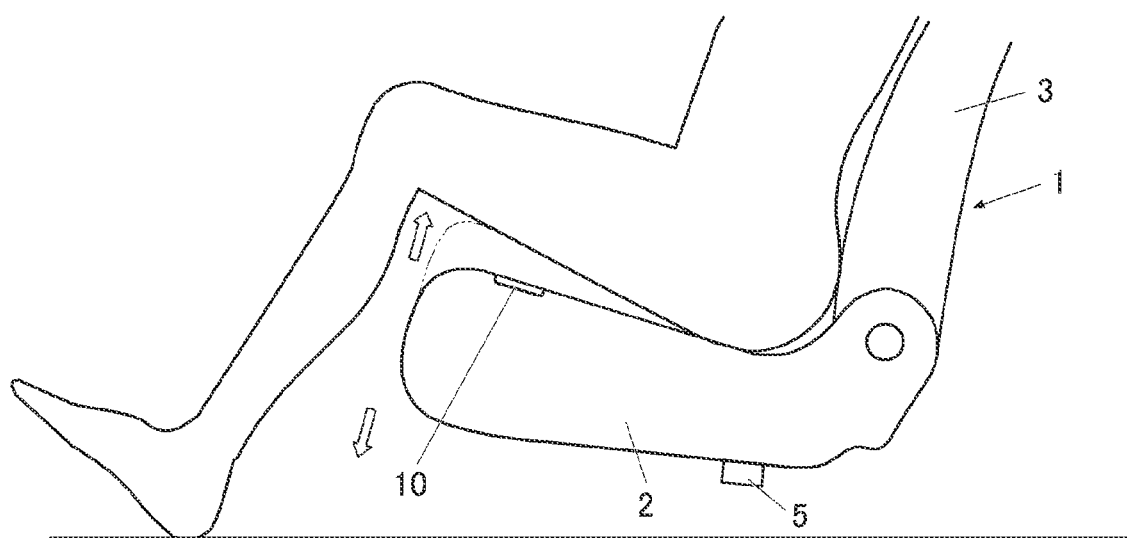
FIG. 8 shows a vehicle seat provided with a cushion tilt mechanism.

As shown in FIG. 8, the control device 5 is attached to the seat 1 as a controller for controlling deformation operation of the seat 1. The control device 5 is attached to a position that does not interfere with operation of components constituting the seat 1 by, for example, screwing it with a bolt.

The control device 5 is also called a so-called ECU (electronic controller). The control device 5 is connected to a driver (such as a motor) and the biological sensor 10 so as to be capable of data communication. The driver operates a mechanism for deforming the seat 1. In other words, the seat 1 and the biological sensor 10 are respectively connected to the control device 5 so as to be capable of data communication. Thereby, a system for acquiring biological information is constructed.

A cushion tilt mechanism is provided on the seat 1 as a device for deforming the seat 1. The cushion tilt mechanism raises and lowers a front end of the seat cushion with respect to a rear end.

That is, the seat cushion 2 of the seat body includes a part that can be moved to adjust a relative position with respect to a body of a seated person. The biological sensor 10 is provided at the part.

The control device 5 is connected to the cushion tilt mechanism so that data communication is possible. The control device 5 controls tilting operation of the front end of the seat cushion 2 provided with the cushion tilt mechanism.

A time for the biological sensor 10 to acquire biological information may be:

any time according to a will of a seated person;

a time registered in advance in the control device 5; and a time when change in physical condition of a seated person is detected.

In a case where biological information is acquired at any time according to a will of a seated person, a button for starting sensing by the biological sensor 10 is provided in the seat 1 or in a vehicle.

The time registered in advance is, for example, time when a person is seated on the seat 1 or time when a vehicle is running. Biological information may be acquired once or multiple times while a vehicle is running. In this case, the seat 1 is provided with a seating sensor (not shown) that detects sitting of a person.

Figure 9:
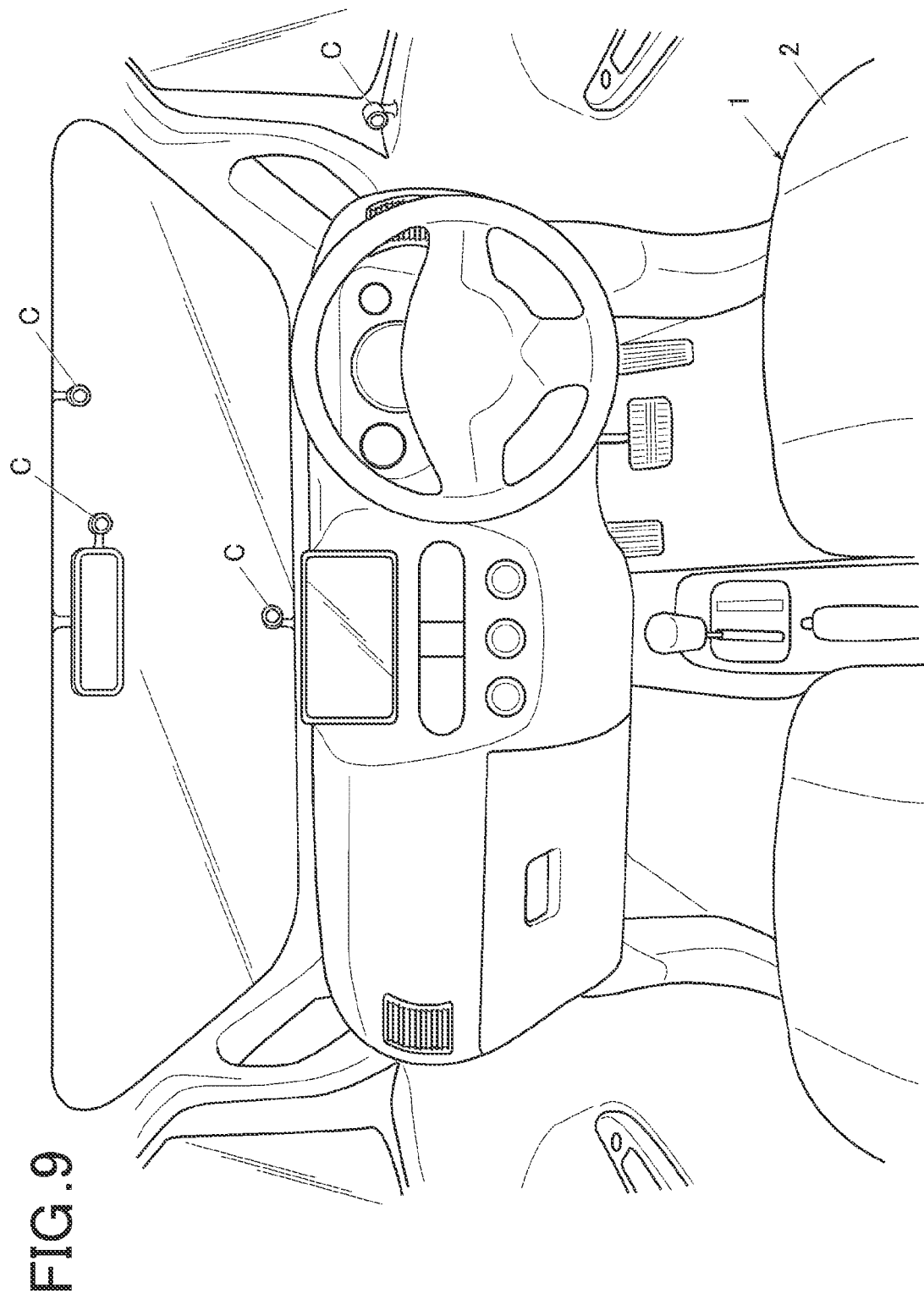
FIG. 9 describes a state inside a vehicle in which a camera is provided.

Change in physical condition of a seated person is detected by, for example, a camera C provided in a vehicle as shown in FIG. 9. In this example, the seated person is set to a driver of the vehicle. Several cameras C are provided around a seat (seat 1) of the driver. More specifically, the cameras C are provided around a windshield and at an edge of a rearview mirror, a front edge of the vehicle door, and the like.

The cameras C are connected to the control device 5 so as to be capable of data communication. The control device 5 stores an image diagnosis program in memory (not shown). The change in physical condition of a seated person is detected from image information taken by the cameras C based on the image diagnosis program.

When it is diagnosed that physical condition of a seated person has changed, the control device 5 controls the biological sensor 10 to begin acquiring biological information.

In the embodiment, the cameras C are used as a means for detecting change in physical condition of a seated person. The means is not limited to this. For example, the means may be a thermometer that detects a temperature of a seated person or a respiration sensor that detects breathing of a seated person.

When it is determined that the biological sensor 10 cannot acquire biological information to be acquired, the control device 5 begins to control operation of a device (in this example, a cushion tilt mechanism). At that time, the biological sensor 10 and a seated person may not be in the optimum positional relation. The control device 5 begins to control operation of the device and optimizes the positional relation between the biological sensor 10 and the seated person.

In a case where it is determined that the biological sensor 10 has acquired biological information to be acquired, the control device 5 does not control operation of the device. The biological sensor 10 continues to acquire biological information.

Figure 10:
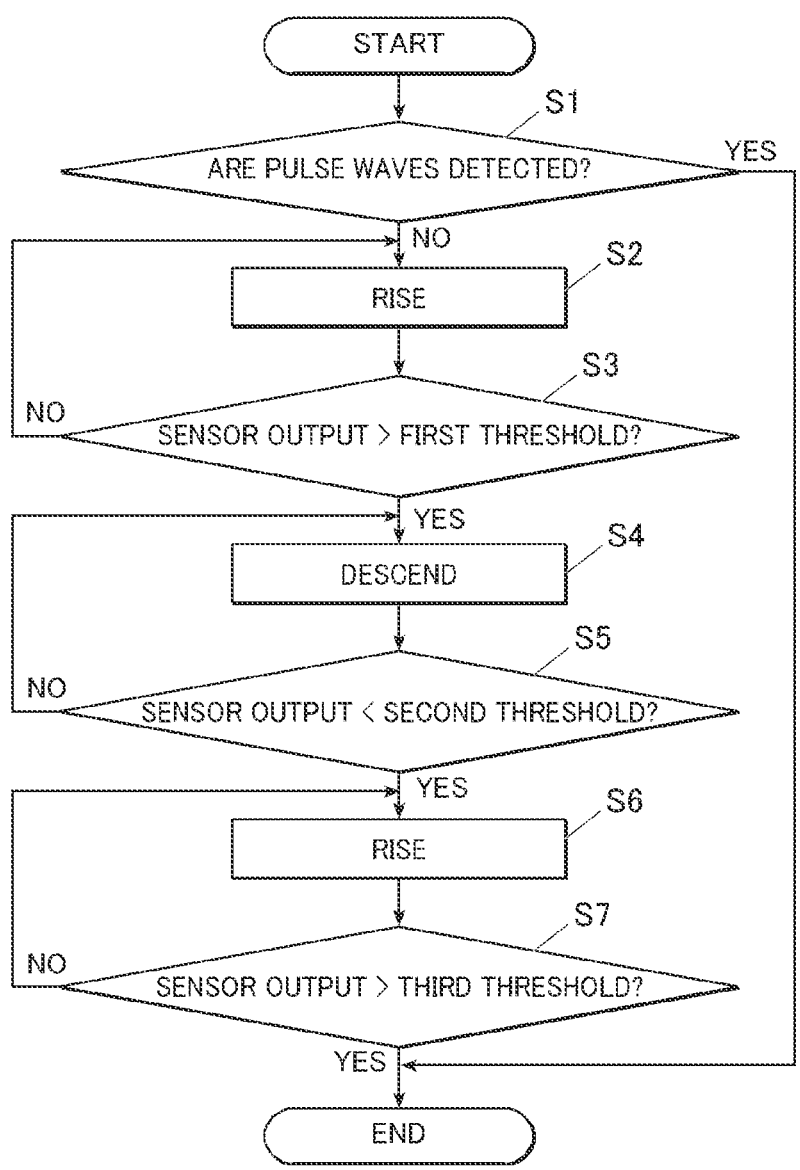
FIG. 10 is a control flow in control of movement of a part of a vehicle seat by a controller.

In control of operation of the device by the control device 5, as shown in FIG. 10, the biological sensor 10 first determines whether biological information (in this embodiment, pulse waves) is detected (Step S1).

In a case where the biological sensor 10 determines in Step S1 that biological information has been detected, operation of the device will not be controlled, and the biological sensor 10 continues to acquire biological information.

In a case where the biological sensor 10 determines in Step S1 that biological information has not been detected, operation of the cushion tilt mechanism will be controlled. The cushion tilt mechanism is the device in the embodiment. More specifically, as shown by a dashed line in FIG. 8, control is performed such that the front end of the seat cushion 2 rises (tilts up) with respect to the rear end (Step S2).

Then, the biological sensor 10 firmly contacts a lower side of a thigh of a seated person at the front end of the seat cushion 2. The biological sensor 10 is pressed so strongly that the seated person feels oppression. A degree to which the oppression is felt is determined based on whether a pressure (value output from the biological sensor 10 to the control device 5, i.e., sensor output) detected by the biological sensor 10 which is a piezoelectric sensor exceeds a preset first threshold value.

Thus, a sensor output is determined in Step S3. In a case where the sensor output exceeds the first threshold, control proceeds to Step S4. In a case where the sensor output is below the first threshold value, operation of tilting up is continued (returning to Step S2).

At a stage of Step S3, the seated person continues to feel oppression. Therefore, in Step S4, the control device 5 performs control such that the front end of the seat cushion 2 descends (tilts down) below the rear end, that is, in a direction away from the lower side of the thigh of the seated person. At this time, the front end of the seat cushion 2 is lowered so as to eliminate the feeling of oppression while contacting the seated person. Elimination of the feeling of oppression is determined based on whether the sensor output falls below a preset second threshold value.

In Step S5, the sensor output is determined. In a case where the sensor output is below the second threshold value, control proceeds to Step S6. In a case where the sensor output exceeds the second threshold value, the operation of tilting down is continued (returning to Step S4).

At the stage of Step S5, something may cause a gap between the biological sensor 10 and the seated person. Therefore, in Step S6, the control device 5 performs control such that the front end of the seat cushion 2 rises (tilts up) above the rear end, that is, in a direction toward the lower side of the thigh of the seated person. At this time, the front end of the seat cushion 2 is raised so as to lightly contact the lower side of the thigh of the seated person. The seated person does not feel oppression. The light contact is determined based on whether the sensor output exceeds a preset third threshold value.

In Step S7, the sensor output is determined. In a case where the sensor output exceeds the third threshold value, the biological sensor 10 begins to acquire biological information. In a case where the sensor output falls below the third threshold value, the operation of tilting up is continued (returning to Step S6).

The control device 5 controls operation of the device as described above. It is possible to determine whether the optimum positional relation between the biological sensor and a seated person is achieved.

Operation of the cushion tilt mechanism by the control device 5 is controlled based on the sensor output of the biological sensor 10.

Therefore, operation is controlled according to a seated person regardless of:
  difference in length of legs between seated persons; and
  difference in length of time for the front end of the seat cushion 2 to come into contact with a lower side of a thigh.

The biological sensor 10 sometimes detects a noise component which is not biological information. In that case, operation of the device may be controlled while monitoring the sensor output to determine whether the optimum positional relation between the biological sensor and a seated person is achieved.

If the biological sensor 10 is prevented from being affected by a noise component, it is not necessary to control operation while monitoring the sensor output as described above. As the biological sensor 10, a biological sensor that can remove noise components and extract only biological information may be used.

The biological sensor that extracts only biological information include at least two sensors that detect vibration. These at least two sensors are layered. Of the at least two sensors, one is the first sensor used to acquire biological information. The other is the second sensor used to remove noise. The first cushion material that attenuates vibration is placed between the first sensor and the second sensor. The first cushion material is layered with the first sensor and the second sensor.

According to such a biological sensor, the first sensor and the second sensor that detect vibration are layered. The same noise which is not biological information is included in each of signals detected by the first sensor and the second sensor. A difference between noise components is taken from biological information including a noise component which is acquired by the first sensor. Thereby, only biological information is extracted. An error in detection of noise components is unlikely to occur between the first and second sensors being layered. Accurate detection of biological information is facilitated.

The first cushion material attenuates vibration transmitted from the first sensor to the second sensor. Therefore, extraction of biological information is facilitated.

The first cushion material prevents contact between the first sensor and the second sensor. Therefore, the first sensor and the second sensor are less likely to be damaged.

According to the present embodiment, the control device 5 controls movement of the part (the front end of the seat cushion 2) that can be moved to adjust a relative position with respect to a body of a seated person. Therefore, positional relation between the biological sensor 10 provided at this part and the seated person is optimized. Accurate detection of biological information is facilitated.

The front end of the seat cushion 2 is operated such that the biological sensor 10 can acquire biological information to be acquired. Accurate detection of biological information is facilitated.

On the contrary, in a case where it is determined that the biological sensor 10 can acquire biological information to be acquired, the control device 5 can prevent the front end of the seat cushion 2 from moving. It prevents unnecessary movement of the front end.

The control device 5 controls operation of the front end of the seat cushion 2 so as to meet conditions of the first to third threshold values. Thereby, the control device 5 determines whether the optimum positional relation between the biological sensor 10 and a seated person is achieved.

The positional relation concerns, for example:
whether the biological sensor 10 is in too strong contact with a seated person;
whether the biological sensor 10 is separated from a seated person; and
whether the biological sensor 10 is in proper contact with a seated person.

The part where the biological sensor 10 is provided and whose movement is controlled by the control device 5 is the front end of the seat cushion which is raised and lowered by the cushion tilt mechanism. The control device 5 controls the front end of the seat cushion 2 to make the biological sensor 10 touch and leave a seated person.

Modification

Hereinafter, a modification of the second embodiment will be described. The following modifications or the above modifications may be combined in possible ways.

Common reference numerals are given to elements common to the above embodiments, the above modifications, and the following modifications. Explanation is omitted or simplified.

Modification 6

Figure 11:
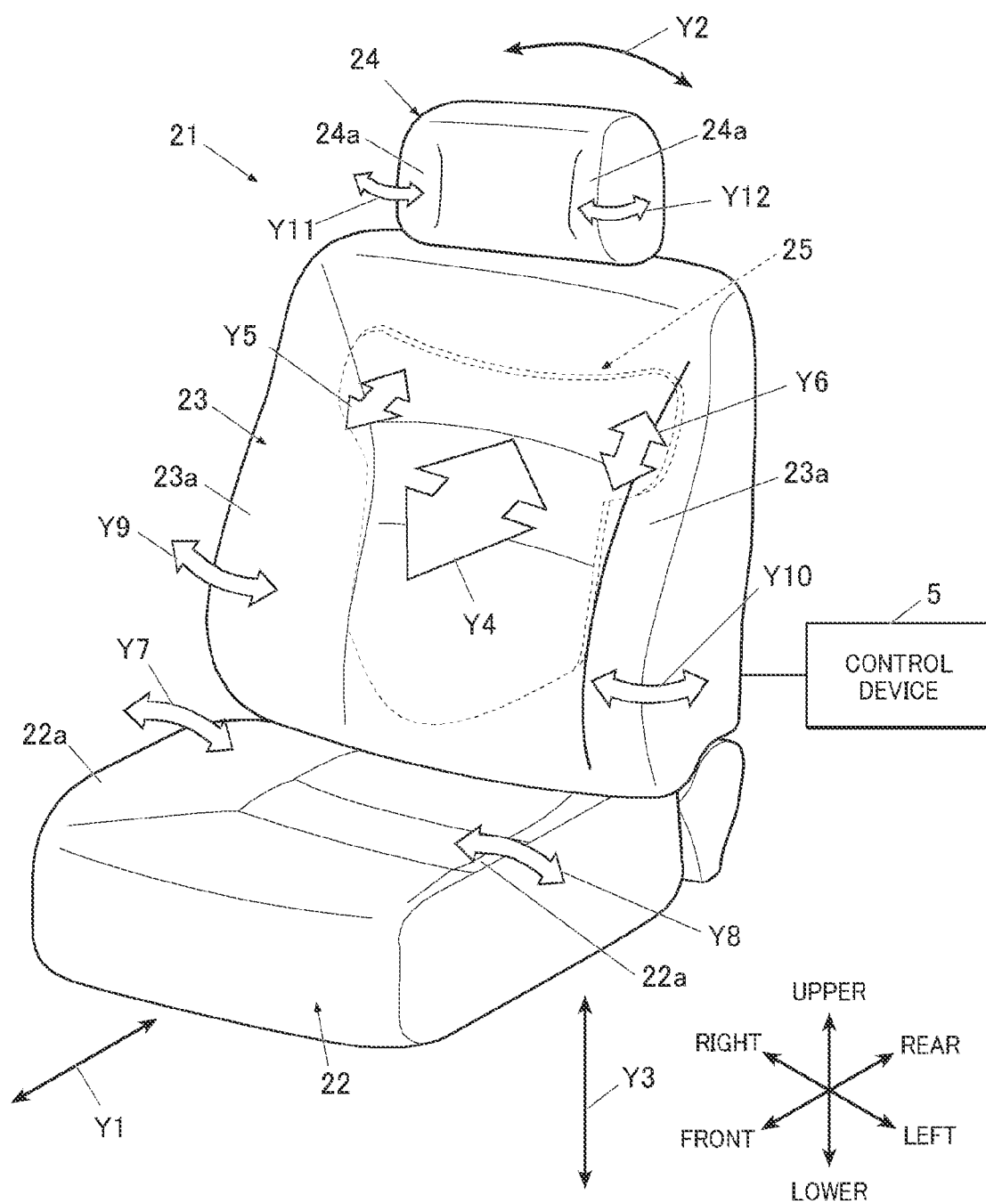

As shown in FIG. 11, a seat 21 in the modification includes a seat cushion 22, a seat back 23, and a headrest 24.

Although not shown, the seat 21 is provided with several biological sensors.

If necessary, the seat 21 further includes:
a slide mechanism that slides the seat 21 in the back and forth directions (see arrow Y1);
a reclining mechanism that changes an angle of the seat back 23 with respect to the seat cushion 22 (see arrow Y2); and
a height mechanism that moves the seat 21 in a vertical direction (see arrow Y3).

A driver (such as a motor) that operates the mechanisms for deforming and moving the seat 1 is connected to the control device 5 so as to be capable of data communication. The control device 5 controls operation of the driver.

A lumbar support 25 is provided inside the seat back 22. The lumbar support 25 can be deformed in the back and forth directions to support a waist of a seated person (see arrows Y4 to Y6).

The lumbar support 25 is connected to the control device 5 so as to be capable of data communication. The control device 5 controls operation of the lumbar support 25.

Banks 22a that bulge upward are provided at both edges of the seat cushion 22 in a width direction. Banks 23a that bulge forward are provided at both edges of the seat back 23 in a width direction. Banks 24a that bulge forward are provided at both edges of the headrest 24 in a width direction.

The banks 22a, 23a, 24a are constituted by frames provided inside the seat cushion 22, the seat back 23, and the headrest 24. The banks 22a, 23a, 24a operate in directions toward and away from a seated person (see arrows Y7 to Y12). Thus, the banks 22a, 23a, 24a are in close contact with a seated person to support a body of the seated person. A driver (such as a motor) that operates the banks 22a, 23a, 24a is connected to the control device 5 so as to be capable of data communication. The control device 5 controls operation of the driver.

The biological sensors are provided at:
a front end of the seat cushion 22;
a front portion of the lumbar support 25; and
a portion of each of the banks 22a, 23a, 24a on a side of a seated person.

All the biological sensors are provided on an inner side of a cover.

Types of the biological sensors provided in the seat 21 may be the same or different.

The biological sensors provided on the front end of the seat cushion 22 and the lumbar support 25 are, for example, pulse wave sensors.

To optimize positional relation between a seated person and the biological sensor provided at the front end of the seat cushion 22, the control device 5 controls operation of the slide mechanism and the height mechanism. That is, the control device 5 makes the biological sensor touch and leave a lower side of a thigh of a seated person.

To optimize the positional relation between a seated person and the biological sensor provided at the lumbar support 25, the control device 5 controls operation of the lumbar support 25 and the reclining mechanism. That is, the control device 5 makes the biological sensor touch and leave a waist and a back of a seated person.

The biological sensors provided at the banks 22a, 23a of the seat cushion 22 and the seat back 23 are, for example, respiration sensors.

To optimize positional relation between a seated person and the biological sensors provided at the banks 22a, 23a, the control device 5 controls operation of the banks 22a, 23a. That is, the control device 5 makes the biological sensors touch and leave a seated person.

The biological sensor provided at the bank 24a of the headrest 24 is, for example, an electroencephalogram sensor.

To optimize positional relation between a seated person and the biological sensor provided at the bank 24a, the control device 5 controls operation of the bank 24a. That is, the control device 5 makes the biological sensor touch and leave a head of the seated person.

According to the modification, the control device 5 controls movement of parts that can be moved to adjust a relative position with respect to a body of a seated person (the front end of the seat cushion 2, the front portion of the lumbar support 25, and the portion of each of the banks 22a, 23a, 24a on the side of a seated person). Therefore, positional relation between the seated person and the biological sensors provided at the parts is optimized. Accurate detection of biological information is facilitated.

The seat 21 in the modification includes several parts where the biological sensors are provided. The control device 5 controls operation of the parts. The seat 21 is not limited to this. The seat 21 may include only one part having such configuration.

Modification 7

Figure 12:
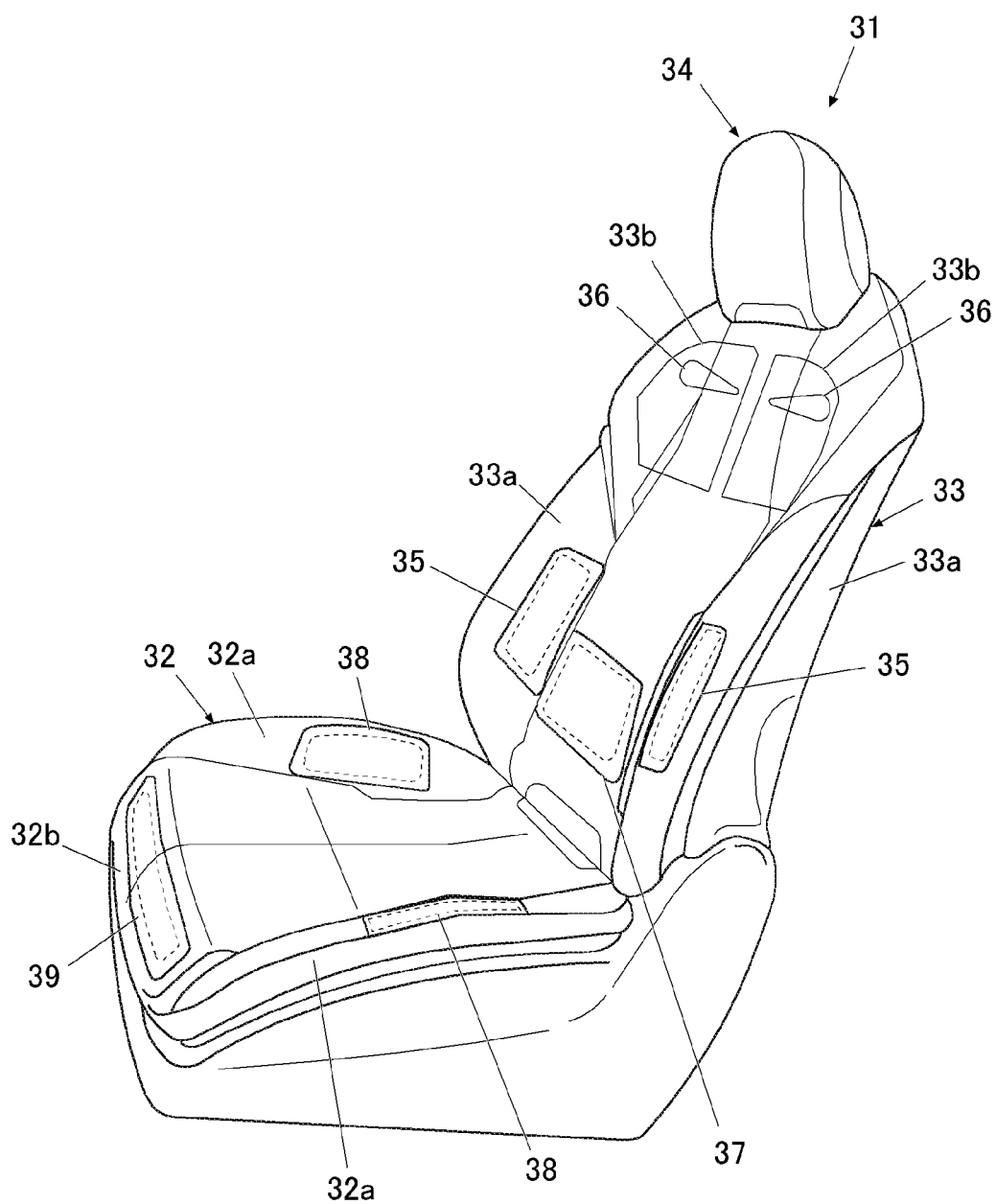
FIG. 12 shows a vehicle seat provided with bags.

As shown in FIG. 12, a seat 31 in the modification includes a seat cushion 32, a seat back 33, and a headrest 34.

Bags 35-39 which are inflated by being filled with fluid are built into various parts of the seat 31. Biological sensors are respectively provided in the bags 35-39 on a side of a seated person.

The bags 35-39 in the modification are air cells 35-39 connected to an air compressor (not shown) which is an air supply source. The bags are not limited to them. The bags may be bags for liquid which are connected to a liquid storage.

Although not shown, the air cells 35-39 may be provided with internal pressure sensors in addition to the biological sensors. The internal pressure sensor measures internal pressures of the air cells 35-39.

Banks 33a that bulge forward are provided at both edges of the seat back 33 in a width direction. An air cell 35 is built into each of banks 33a. The air cell 35 has a function of pushing a side of a seated person forward by bulging.

The seat back 33 includes shoulder supports 33b that support shoulders of a seated person. An air cell 36 is built into the shoulder support 33b. The air cell 36 has a function of pushing a shoulder of a seated person downward and inward in a width direction by bulging.

An air cell 37 is provided in the seat back 33 at a position corresponding to a waist of a seated person. The air cell 37 has a function of pushing a waist of a seated person, especially a back side, forward.

That is, around a waist, the left and right air cells 35 and the back side air cell 37 support a waist of an occupant from three sides. For optimal waist support, support pressures of the left and right air cells 35 are adjusted according to an amount of bulge of the air cell 37 on the back side.

Banks 32a that bulge upward are provided at both edges of the seat cushion 32 in the width direction. An air cell 38 is built into each of the banks 32a. The air cell 38 has a function of pushing buttocks and thighs of a person seated on the seat 31 inward in a width direction by bulging.

An ottoman 32b is provided at a front end of the seat cushion 32. The ottoman 32b serves as a below-knee support that supports a portion of a leg of a seated person below a knee. The ottoman 32b includes an air cell 39 placed at the front end of the seat cushion 32. The ottoman 32b has a function of supporting a leg of a seated person below a knee from below when the air cell 39 bulges.

To optimize positional relation between a seated person and the biological sensors provided on the air cells 35-39 on the side of the seated person, the control device 5 controls operation of an air compressor that inflates the air cells 35-39. That is, the control device 5 makes the biological sensors touch and leave a seated person.

According to the modification, the control device 5 controls movement of the parts (air cells 35-39) that can be moved to adjust relative positions with respect to a body of a seated person. Positional relation between a seated person and the biological sensors provided at the parts is optimized. Accurate detection of biological information is facilitated.

Modification 8

Figure 13:
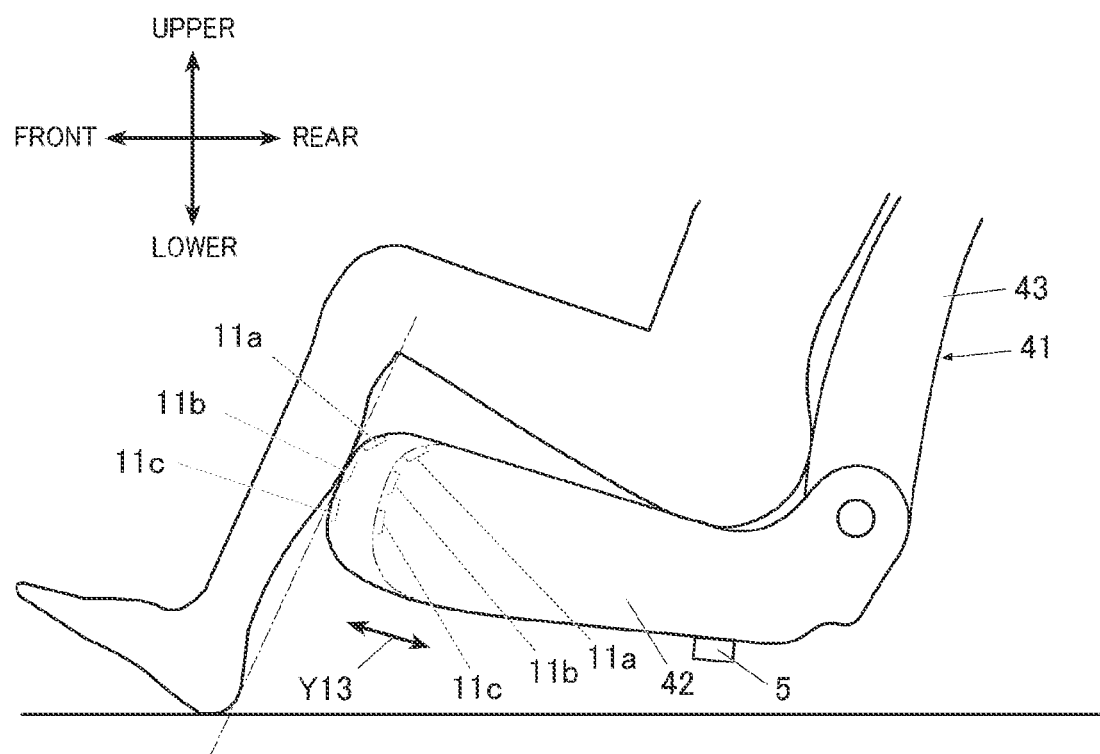
FIG. 13 shows a vehicle seat provided with a cushion front-rear length adjustment mechanism.

As shown in FIG. 13, a seat 41 in the modification includes a seat cushion 42 and a seat back 43.

Biological sensors 11a, 11b, 11c which are, for example, pulse wave sensors are provided on an inner side of a cover at a front end of the seat cushion 42.

The seat cushion 42 includes a cushion front-rear length adjustment mechanism. The cushion front-rear length adjustment mechanism adjusts a length in back and forth directions by moving the front end of the seat cushion 42 in the back and forth directions with respect to a rear end. See arrow Y13 in FIG. 13.

A driver (such as a motor) that operates the cushion front-rear length adjustment mechanism is connected to the control device 5 so as to be capable of data communication. The control device 5 controls operation of the driver.

The control device 5 controls operation of the cushion front-rear length adjustment mechanism to optimize positional relation between:

one of the biological sensors 11a, 11b, 11c provided at the front end of the seat cushion 42; and
a seated person.

That is, the control device 5 makes one of the biological sensors 11a, 11b, 11c touch and leave a calf of a seated person.

According to the modification, the control device 5 controls movement of the part (the front end of seat cushion 42) in the back and forth directions, the part being able to be moved to adjust relative position with respect to a body of a seated person. Positional relation between a seated person and the biological sensors 11a, 11b, 11c provided at the part is optimized. Accurate detection of biological information is facilitated.

Modification 9

Figure 14A:
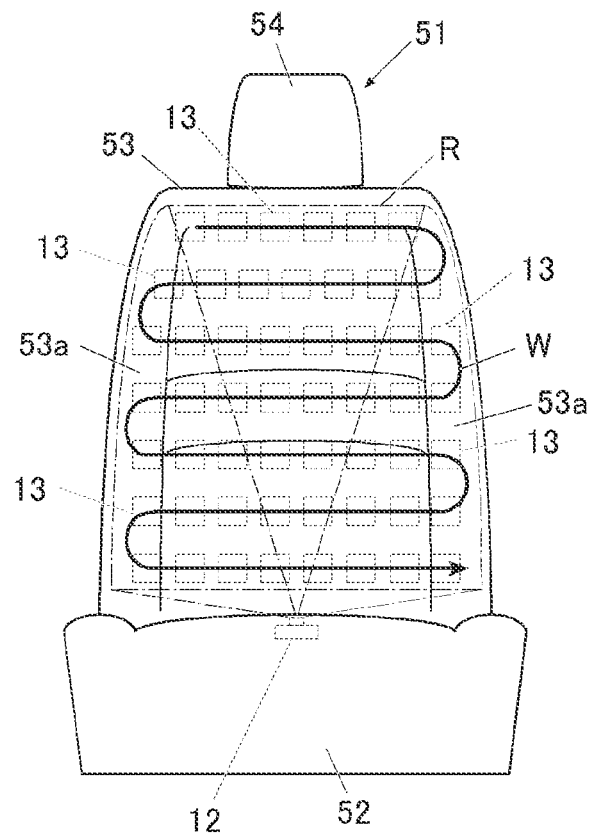
FIG. 14A illustrates a build detection sensor provided in a vehicle seat.
Figure 14B:
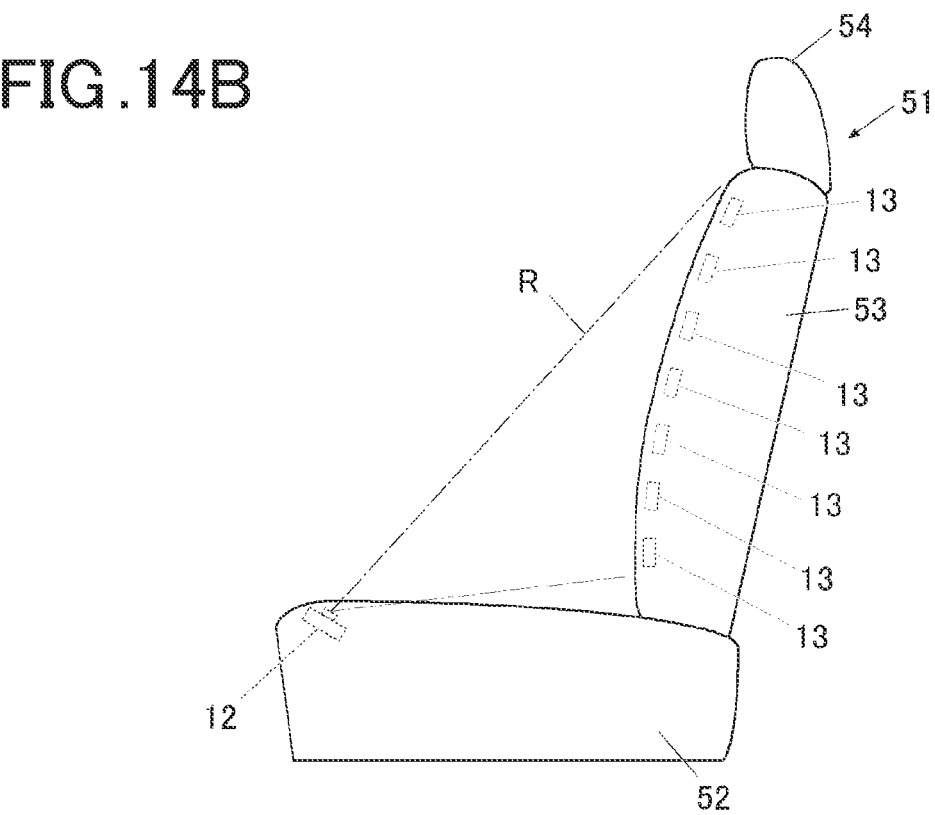
FIG. 14B illustrates a build detection sensor provided in a vehicle seat.

As shown in FIGS. 14A to 14B, a seat 51 in the modification includes a seat cushion 52, a seat back 53, and a headrest 54.

A biological sensor (not shown) is provided in at least one of the seat cushion 52 and the seat back 53. Further, in the modification, in addition to the biological sensor, a build detection sensor for detecting a build of a seated person is provided.

The biological sensor 10 in the modification is a pulse wave sensor provided at the front end of the seat cushion 52.

The build detection sensor is a build measurer that measures a build of a seated person, and is connected to the control device 5 so as to be capable of data communication.

The build detection sensor includes:

a transmitter 12 which is provided in the seat cushion 52 and which irradiates the seat back 53 with electromagnetic waves W in a scanning line; and receivers 13 which are provided in a grid pattern in the seat back 53 and which receive the electromagnetic waves W emitted from the transmitter 12.

The receivers 13 are arranged in a grid pattern within an irradiation range R which can be irradiated by the transmitter 12 with the electromagnetic waves W.

The transmitter 12 and the receivers 13 are provided on inner sides of covers of the seat cushion 52 and the seat back 53.

When the build detection sensor measures a build of a seated person, the electromagnetic waves W are emitted from the transmitter 12 toward the receivers 13. Strength of the electromagnetic waves W reaching the receiver 13 varies depending on a thickness of a body of a seated person. In a case where the electromagnetic waves W are received by the receiver 13 without passing through a body of a seated person, it is determined that the body of the seated person is not at a position of the receiver 13.

Thus, the build detection sensor detects an approximate build (upper body) of the seated person.

The control device 5 estimates a body width, a body thickness, a sitting height, etc. from information (build detection information) obtained from the build detection sensor. Based on estimation result, the control device 5 operates a driver that operates a mechanism for deforming the seat 51.

For example, in a case where banks 53a in the seat back 53 move in directions toward and away from a seated person, the control device 5 makes the banks 53a touch and leave a body of a seated person based on build detection information of the seated person.

According to the modification, a build of an upper body of a seated person can be detected. The controller 5 can control movement of the part provided with the biological sensor based on the build detection information. More accurate detection of biological information is facilitated.

Third Embodiment

Next, a third embodiment of the present invention will be described with reference to the drawings. For convenience of explanation, the same reference numerals are given to components common to the first and second embodiments and the third embodiment. Components different from the first and second embodiments will be mainly described. Duplicate explanations are given when necessary.

According to blood pressure measurement without a cuff (i.e., without using a cuff type manometer) based on pulse wave transit time and the like, difference among individuals is large. Calibration using a cuff type manometer is required depending on a person to be measured. However, it is basically difficult to install a cuff type manometer to a vehicle. In a case where a biological sensor that detects biological information is installed in a vehicle, vibration from the vehicle tends to generate noise. Since biological information is unlikely to be detected accurately, a reference value for blood pressure calculation may be incorrectly calculated.

In view of this, the third problem is to facilitate acquisition of accurate biological information by performing calibration according to a subject for a cuffless blood pressure measurement device installed in a vehicle.

To solve such a problem, the twenty-first invention shown in an embodiment is a biological information acquisition system, including:
  a first measurer and a second measurer each of which acquires biological information of a person; and
  a calibrator that receives:
    data of a first measurement value of the biological information measured by the first measurer; and
    data of a second measurement value of the biological information measured by the second measurer,
  wherein
  the calibrator calibrates the second measurement value with reference to the first measurement value, and
  at least the second measurer of the first measurer and the second measurer is provided in a vehicle which the person rides.

The twenty-second invention shown in the embodiment is the biological information acquisition system according to the twenty-first invention, wherein
  the first measurer is outside the vehicle, and
  the second measurer is in the vehicle.

The twenty-third invention shown in the embodiment is the biological information acquisition system according to the twenty-first or twenty-second invention, wherein the second measurer is provided in a seat on which the person in the vehicle sits.

The twenty-fourth invention shown in the embodiment is the biological information acquisition system according to the twenty-first invention, wherein
  the first measurer and the second measurer are in the vehicle, and
  the second measurer is provided in a seat in the vehicle on which the person sits.

The twenty-fifth invention shown in the embodiment is the biological information acquisition system according to the twenty-third or twenty-fourth invention, wherein
  the first measurer is a manometer including a cuff that winds around a limb of the person, and
  the second measurer is biological sensors provided at at least two positions in the seat.

The twenty-sixth invention shown in the embodiment is the biological information acquisition system according to any one of the twenty-first to twenty-fifth inventions, wherein the first and second measurement values include identification information that identifies the person.

The twenty-seventh invention shown in the embodiment is the biological information acquisition system according to any one of the twenty-first to twenty-sixth inventions, wherein
  the calibrator is provided in the vehicle,
  the second measurer and the calibrator are communicably connected, and
  data of the first measurement value acquired by the first measurer is transmitted to the calibrator through a computer network.

The twenty-eighth invention shown in the embodiment is the biological information acquisition system according to any one of the twenty-first to twenty-sixth inventions, wherein
  the calibrator is provided in an information terminal that performs short range wireless communication with the first measurer and the second measurer, and
  data of the first measurement value acquired by the first measurer and data of the second measurement value acquired by the second measurer are transmitted to the information terminal by the short range wireless communication.

The twenty-ninth invention shown in the embodiment is the biological information acquisition system according to any one of the twenty-first to twenty-sixth inventions, wherein
  the calibrator is provided in an information terminal that performs short range wireless communication with the second measurer,
  data of the first measurement value acquired by the first measurer is transmitted to the information terminal through a computer network, and
  data of the second measurement value acquired by the second measurer is transmitted to the information terminal by the short range wireless communication.

The thirtieth invention shown in the embodiment is a biological information acquisition method for a first measurer and a second measurer that acquire biological information of a person, at least one of the first and second measurers being provided in a vehicle which a person rides, the method comprising:
  measuring the person by the first measurer and then measuring the person by the second measurer, and
  calibrating a second measurement value of the biological information measured by the second measurer with reference to a first measurement value of the biological information measured by the first measurer by a calibrator that receives the first and second measurement values.

According to the twenty-first and thirtieth inventions, the first measurer not provided in a vehicle does not receive vibration from the vehicle. The second measurement value of biological information of a person on board is calibrated with reference to the first measurement value, which is not affected by vehicle vibration. As a result, detection of accurate biological information is facilitated.

Even if both the first measurer and the second measurer are provided in a vehicle, the second measurement value is calibrated with reference to the first measurement value. Detection of more accurate biological information is facilitated as compared with a case where, for example, biological information of a person is acquired using only one of the first measurer and the second measurer.

According to the twenty-second invention, the first measurer is not subject to vibration from the vehicle. The second measurement value of biological information of a person on board is calibrated with reference to the first measurement value, which is not affected by vehicle vibration. Detection of accurate biological information is facilitated.

According to the twenty-third invention, the second measurer is provided in the seat in a vehicle on which a person sits. Biological information is acquired and the second measurement value is calibrated not only when a person is in the vehicle but also when the person is driving the vehicle.

According to the twenty-fourth invention, detection of more accurate biological information is facilitated as compared with a case where, for example, biological information of a person is acquired using only one of the first measurer and the second measurer. Biological information is acquired and the second measurement value is calibrated not only when a person is in the vehicle but also when the person is driving the vehicle.

If both the first measurer and the second measurer are provided in the vehicle, it is not necessary to provide either one outside the vehicle. The system is aggregated. Efficiency of maintenance and the like is improved.

According to the twenty-fifth invention, the first measurer is a manometer including a cuff that winds around a limb of the person.
Measurement is made with the cuff being as close to a heart as possible in a resting state. Thereby, detection of an accurate blood pressure is facilitated.

The second measurer is biological sensors provided at at least two positions in the seat. For example, both biological sensors are pulse wave sensors. Alternatively, one biological sensor is an electrocardiograph and the other biological sensor is a pulse wave sensor. A blood pressure is estimated by known methods using pulse wave transit time.

The second measurement value is then calibrated with reference to the first measurement value. Detection of more accurate biological information is facilitated.

According to the twenty-sixth invention, the first and second measurement values include identification information that identifies a person. Biological information for each person can be acquired.

According to the twenty-seventh invention, the data of the first measurement value acquired by the first measurer is transmitted to the calibrator provided in a vehicle through the computer network. The second measurer and the calibrator are communicably connected. The second measurement value is calibrated with reference to the first measurement value even while the vehicle is running, for example, at a place far away from the first measurer. Accurate biological information can be acquired.

According to the twenty-eighth invention, the calibrator is provided in the information terminal. The information terminal performs short range wireless communication with the first measurer and the second measurer. The data of the first measurement value is transmitted to the information terminal in advance by short range wireless communication. The second measurement value is calibrated with reference to the first measurement value even while the vehicle is running, for example, at a place far away from the first measurer. Accurate biological information can be acquired.

According to the twenty-ninth invention, the calibrator is provided in the information terminal that performs short range wireless communication with the second measurer. The data of the first measurement value acquired by the first measurer is transmitted to the calibrator provided in the information terminal through the computer network. The second measurement value is calibrated with reference to the first measurement value even while the vehicle is running, for example, at a place far away from the first measurer. Accurate biological information can be acquired.

Embodiments will be described in more detail with Examples 1-3.

Example 1

Figure 15:
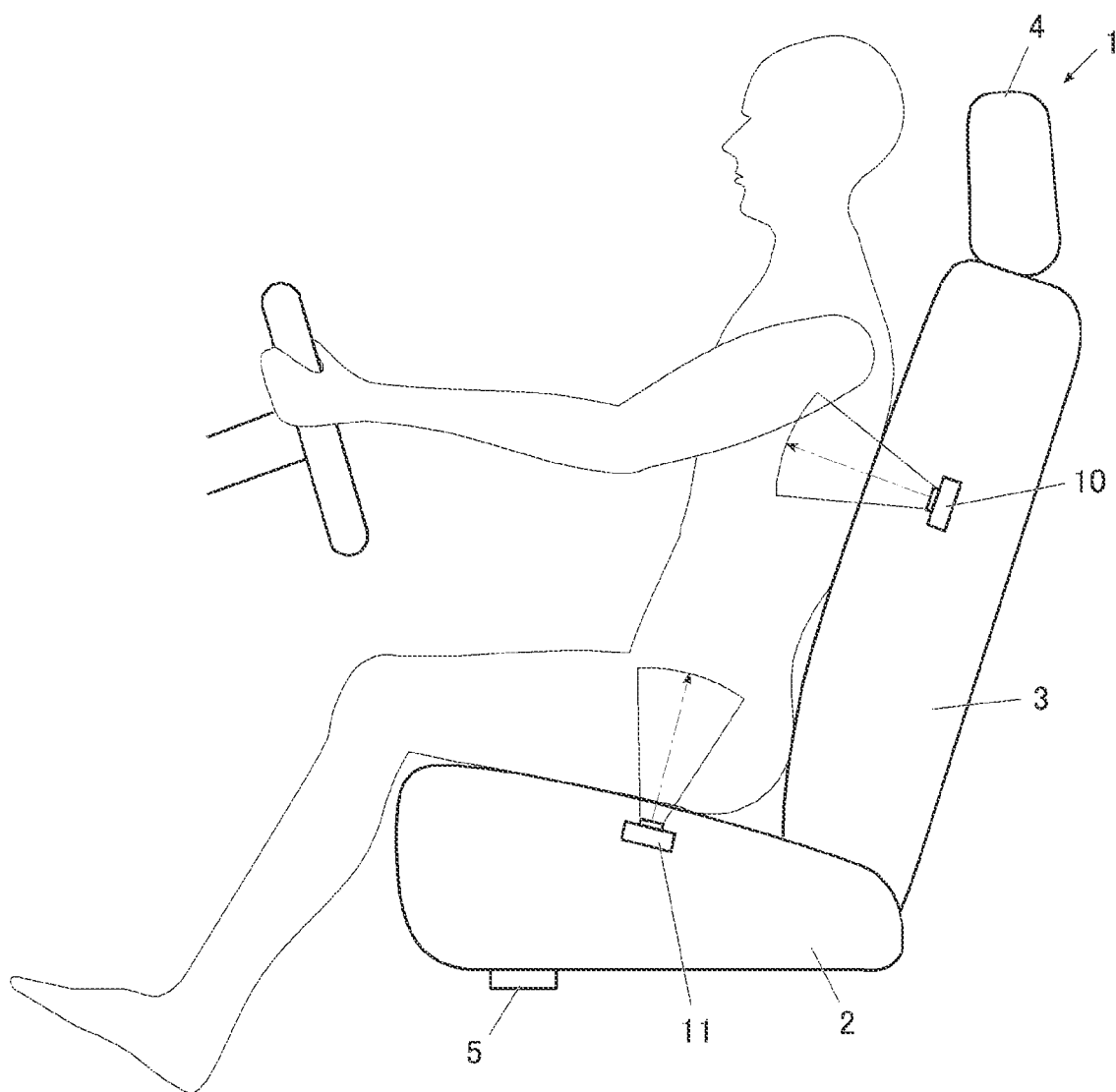
FIG. 15 shows a state in which biological sensors are provided at two positions in a seat.

In FIG. 15, reference numeral 1 indicates a vehicle seat (hereinafter referred to as "seat 1") on which a person sits. The seat 1 is provided in a vehicle such as an automobile. The vehicle may travel while being driven only manually. Alternatively, the vehicle may travel while switching between automatic driving and manual driving.

The seat 1 includes:
 a seat cushion 2 that supports buttocks and thighs of a person;
 a seat back 3 which serves as a backrest and which has a lower end supported by the seat cushion 2; and
 a headrest 4 provided on the seat back 3 to support a head of a person.

The seat cushion 2 mainly includes:
 a seat cushion frame that is a skeleton;
 a cushion pad provided on the seat cushion frame; and
 a cover that covers the seat cushion frame and the cushion pad.

The seat back 3 mainly includes:
 a seat back frame that is a skeleton;
 a cushion pad provided on the seat back frame; and
 a cover that covers the seat back frame and the cushion pad.

The seat 1 is provided with biological sensors 10, 11, that is, the second measurers. The biological sensors 10, 11 serve as a means for recognizing health condition of a seated person (living body). More specifically, the biological sensors 10, 11 in the first Example 1 detect pulse waves as biological information from a blood flow at a position opposite to a skin surface of the seated person.

In Example 1, a position of one biological sensor 10 corresponds to a position of a heart (thoracic aorta) of the seated person. It is provided in the cushion pad of the seat back 3 on a side of the seated person and on an inner side of the cover. A position of the other biological sensor 11 corresponds to a position of buttocks (center of left and right ischia) or thighs of the seated person. The biological sensor 11 is provided in the seat cushion 2 on an upper side of the cushion pad and on an inner side of the cover.

The biological sensor 10 corresponding to the position of the heart of the seated person may be an electrocardiographic sensor that takes an electrocardiogram of the seated person.

The biological sensors 10, 11 that detect pulse waves are, for example:
 photoelectric pulse wave sensors that measure pulse waves of a seated person using light;
 piezoelectric pulse wave sensors that measure pulse waves of a seated person by measuring pressure waves on a body surface of the seated person; or
 electromagnetic wave type pulse wave sensors that measure pulse waves of a seated person using electromagnetic waves.

In Example 1, any of those types of pulse wave sensors may be adopted. Those types of pulse wave sensors may be used in combination.

The seat 1 is provided with the control device 5. The control device 5 is connected to each of the biological sensors 10, 11 by a harness or the like so as to be capable of data communication. The control device 5 in Example 1 is provided at a lower part of the seat 1. Thus, the control device 5 is provided in a vehicle.

The control device 5 is also called a so-called ECU (electronic controller). The control device 5 functions as a blood pressure estimation unit that estimates a blood pressure of a seated person from pulse waves (electrocardiogram) acquired by the biological sensors 10, 11. Memory (not shown) in the control device 5 stores a blood pressure estimation program. The control device 5 calculates and derives data related to an estimated value of a blood pressure of a seated person (i.e., the second measurement value) based on the blood pressure estimation program. Thus, the control device 5 together with the biological sensors 10, 11 function as the second measurer.

More specifically, a blood pressure is estimated using a known blood pressure estimation method based on pulse wave transit time on the basis of:
  a distance between two points where the biological sensors 10, 11 are placed; and
  a difference in time of sensing pulse waves between the two points where the biological sensors 10, 11 are placed.

The blood pressure estimation program is created based on the blood pressure estimation methods, and is executed by the control device 5.

In other words, as shown in FIG. 15, the biological sensors 10, 11 are arranged at at least two different positions in the seat 1. Thereby, pulse wave data is detected from the at least two positions on a body of a seated person. Accuracy of calculation of health condition of a seated person by estimating a blood pressure from detected pulse wave data is improved as compared with a case where only one biological sensor is used.

Figures 16A, 16B:
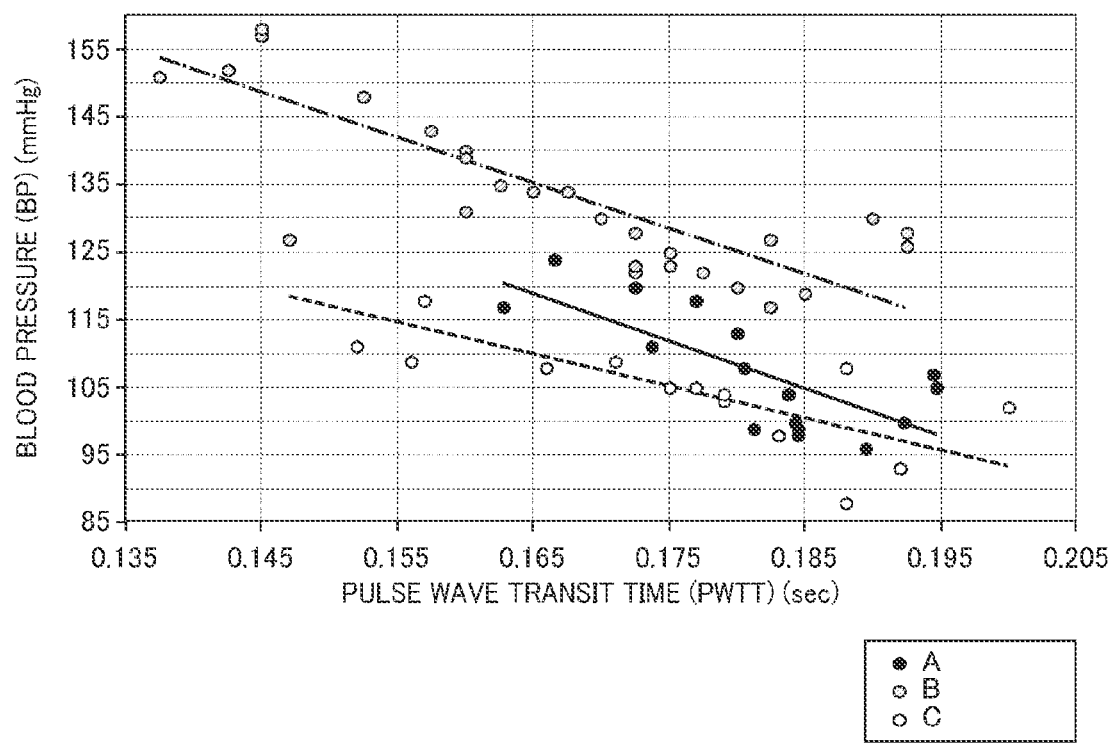
FIG. 16A is a graph and a table showing experimental data of a blood pressure estimation method using pulse wave transit time.
FIG. 16B is a graph and a table showing experimental data of the blood pressure estimation method based on pulse wave transit time.

As shown by experimental data of FIGS. 16A to 16B, according to the blood pressure estimation method based on pulse wave transit time, difference among individuals tends to be large. Data of one person tends to vary. Further, data tends to be affected by vibration of a vehicle.

Figure 17:
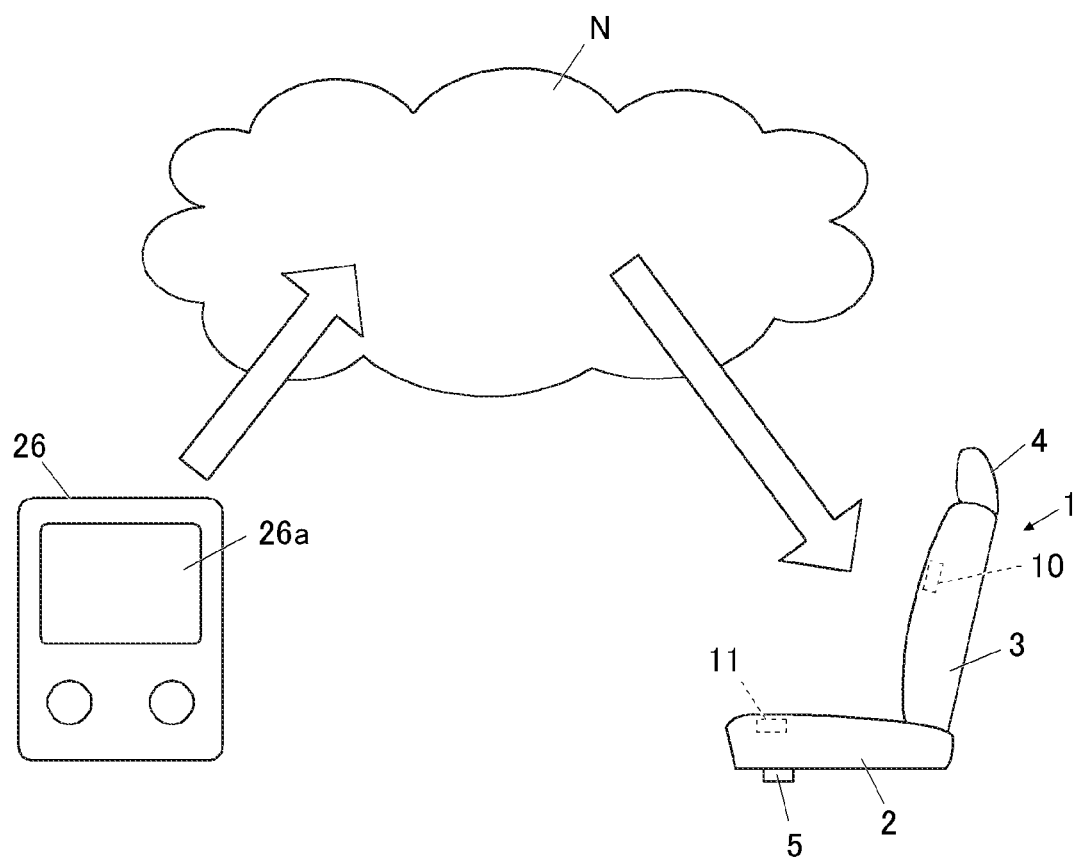
FIG. 17 describes a method of acquiring biological information using a computer network.

According to Example 1, an accurate blood pressure can be easily derived by using the blood pressure estimation method based on pulse wave transit time even while a person is in a vehicle. To achieve this, as shown in FIG. 17, a blood pressure is measured several times in advance by a manometer 26 including a cuff 21 (see FIG. 23) that can be worn on a limb of a person (hereafter called a cuff type manometer 26). The control device 5 uses blood pressure measurement value data measured by the manometer as a reference. The control device 5 calibrates the blood pressure estimation value data estimated in the blood pressure estimation method based on pulse wave transit time.

Thus, the control device 5 functions as a calibrator that calibrates the blood pressure estimation value data with reference to the blood pressure measurement value data.

More specifically, memory of the control device 5 stores a calibration program for realizing a function as the calibrator. The control device 5 calibrates the blood pressure estimation value data with reference to the blood pressure measurement value data based on the calibration program.

Such a calibration program makes the control device 5, which is a computer, function as the calibrator. The calibrator calibrates the data of the second measurement value with reference to the data of the first measurement value. The first measurement value relates to biological information of a person which is measured by the first measurer that acquires the biological information. The second measurement value relates to biological information of a person which is measured by the second measurer that acquires the biological information.

Thus, the control device 5 also functions as the second measurer and the calibrator as described above.

The control device 5 further includes a communicator for connecting to a computer network such as the Internet N. The control device 5 connects to a server (not shown) that supports cloud computing via the Internet N.

The blood pressure estimation value data includes a pulse wave transit time (PWTT). The blood pressure estimation value data includes identification information that identifies an individual. Means for identifying an individual is not particularly limited.

For example, an individual is identified by:
  transmission of ID (identification information) of a seated person to the control device 5;
  input of information by a seated person;
  use of a seating sensor that measures a weight; or
  use of other personal authentication means.

Equipment and functions necessary for identifying an individual are provided in a vehicle.

The cuff type manometer 26, that is, the first measurer adopts a method of indirect measurement (also called an indirect method, non-invasive type, or non-operative type). In Example 1, the cuff type manometer 26 is an automatic manometer capable of mechanical measurement.

A body of the cuff type manometer 26 includes at least:
  a display 26a that displays a blood pressure;
  a pump (not shown) that sends air to a cuff 27; and
  a communicator (not shown) that transmits data to the outside.

The communicator uses a computer network such as the Internet N to transmit blood pressure measurement value data, that is, the first measurement value to the outside.

As shown in FIG. 17, the communicator in Example 1 transmits a blood pressure measurement value to a server (not shown) that supports cloud computing via the Internet N.

The blood pressure measurement value data measured by the cuff type manometer 26 includes identification information that identifies an individual. Means for identifying an individual is not particularly limited.

For example, an individual is identified by:
  transmitting ID (identification information) to the cuff type manometer 26;
  reading ID constituted by barcode or the like;
  entering information oneself; or
  using other personal authentication means.

The cuff type manometer 26 or a peripheral device has a function necessary for identifying an individual.

The cuff 27 is a compression band that winds around a limb of a person. The cuff 27 is inflated by pumping air from the pump of the manometer body. An acoustic sensor such as a microphone built into the cuff 27 detects a blood pressure.

The manometer body and the cuff 27 are connected by:
  a connection line that transmits sensing information from the acoustic sensor to the manometer body; and
  an air supply tube 27a (see FIG. 23) that sends air from the pump of the manometer body to the cuff 27.

In Example 1, the cuff type manometer 26 is outside a vehicle. Specifically, the cuff type manometer 26 is at a home of a person sitting on the seat 1. The location is not limited to this. The cuff type manometer 26 may be placed in a medical institution such as a hospital, or may be placed in another place.

That is, the cuff type manometer 26 may be placed at any place outside a vehicle where:
- the cuff type manometer 26 can be placed;
- a computer network can be used; and
- individuals can be identified.

A method of acquiring a blood pressure of a seated person, i.e., biological information, using the cuff type manometer 26 and the biological sensors 10, 11 will be described.

Figure 18:
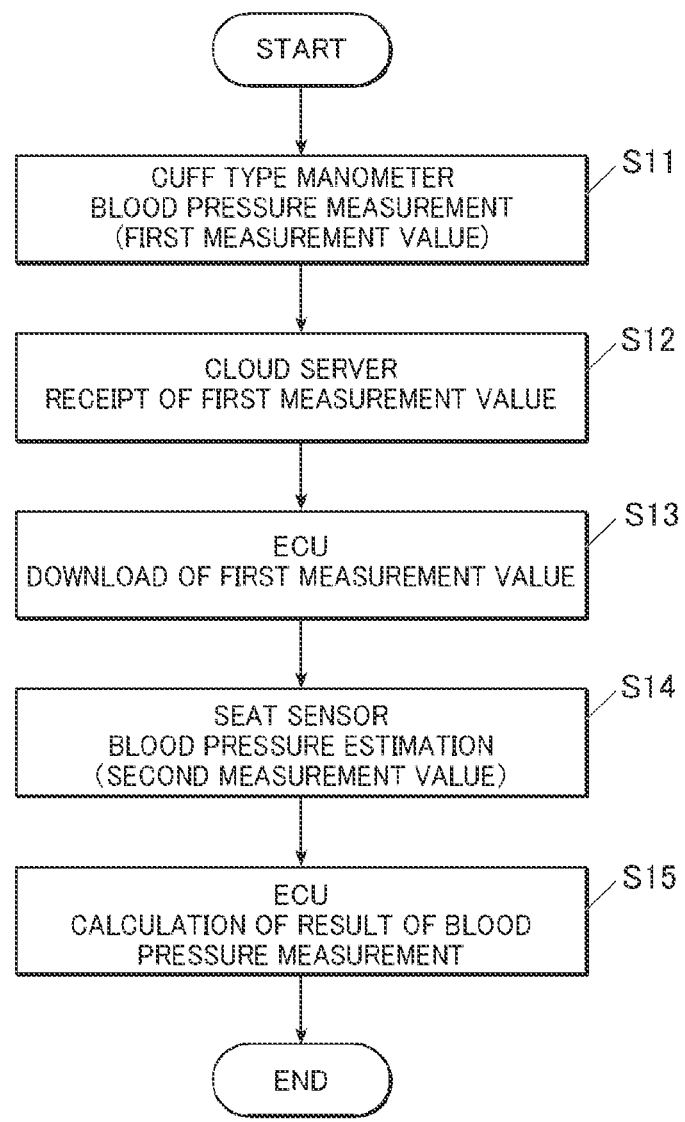
FIG. 18 is a flowchart illustrating the method of acquiring biological information using the computer network.

As shown in FIG. 18, first, a person (seated person) measures a blood pressure with the cuff type manometer 26 outside a vehicle, in Example 1, at home (Step S11). Thereby, blood pressure measurement value data, which is the first measurement value, is derived.

The communicator of the cuff-type manometer 26 transmits the blood pressure measurement value data to the server that supports cloud computing via the Internet N (Step S12).

The control device 5 provided in a vehicle downloads the blood pressure measurement value data from the server via the Internet N (Step S13).

Time for the control device 5 to download the blood pressure measurement value data may be:
- time right after the communicator of the cuff type manometer 26 transmits the blood pressure measurement value data to the server;
- time when a person sits on the seat 1; or
- time for the biological sensors 10, 11 to estimate a blood pressure after a person sits.

A blood pressure of a seated person is estimated in a known blood pressure estimation method based on pulse wave transit time with the biological sensors 10, 11 provided in the seat 1 (Step S14). Thereby, the blood pressure estimation value data (pulse wave transit time), which is the second measurement value, is derived.

After the blood pressure estimation value data is derived, the control device 5 calibrates the blood pressure estimation value data with reference to the downloaded blood pressure measurement value data. The control device 5 calculates result of blood pressure measurement (Step S15). Thus, a "current" blood pressure of a person sitting on the seat 1 is derived more accurately based on the blood pressure measurement value data.

In Example 1, the control device 5 calibrates the blood pressure estimation value data estimated in the blood pressure estimation method based on pulse wave transit time using the blood pressure measurement value data measured by the cuff type manometer 26. An expression for the calibration is as follows.

$$BP = \alpha \times PWTT + \beta \qquad \text{Expression}$$

BP is a blood pressure to be derived, and the unit is "mmHg". PWTT is a pulse wave transit time, and the unit is "sec", i.e., "second".

Letters "$\alpha$" and "$\beta$" are parameters for a person. The blood pressure measurement value data is measured by the cuff type manometer 26 which is the first measurer. Values based on the blood pressure measurement data is applied to a and D. Explanation will be given with reference to FIGS. 16A to 16B. The blood pressure measurement value data is obtained by measuring a blood pressure of a person several times with the cuff type manometer 26. The letter "$\alpha$" is an approximate straight line (i.e., a slope) derived from the blood pressure measurement value data. The letter "$\beta$" is a measurement value of blood pressure, that is, an intercept. In FIGS. 16A to 16B, $\alpha$ is "−705" and $\beta$ is "+235" for "Mr. A". For "Mr. B", $\alpha$ is "−670" and S is "+245". For "Mr. C", $\alpha$ is "−472" and $\beta$ is "+188".

For example, "Mr. A" is a seated person. After Mr. A sits on the seat 1 of the vehicle, the pulse wave transit time "PWTT" is derived by the biological sensors 10, 11. By applying them to the above expression, a calibrated blood pressure value is calculated. For example, in a case where the pulse wave transit time "PWTT" derived by the biological sensors 10, 11 is 0.160 sec, a blood pressure is calculated as 122.2 mmHg.

Thus, a blood pressure of a seated person is acquired.

In Example 1, biological information of a person acquired by the biological information acquisition system is a blood pressure. The biological information is not limited to this. For example, biological information such as body temperature may be acquired.

According to Example 1, the cuff type manometer 26 not provided in a vehicle does not receive vibration from the vehicle. Therefore, the blood pressure estimation value data related to biological information of a person on board, that is, a subject of the cuffless blood pressure measurement device, is calibrated with reference to the blood pressure measurement value data not affected by vehicle vibration. As a result, detection of accurate biological information is facilitated.

Even in a case where both the cuff type manometer 26 and the biological sensors 10, 11 are installed in a vehicle, the blood pressure estimation value data is calibrated with reference to the blood pressure measurement value data. Detection of more accurate biological information is facilitated as compared with a case where, for example, a blood pressure of a person is acquired using only one of the cuff type manometer 26 and the biological sensors 10, 11.

The cuff type manometer 26 is not subject to vibration from a vehicle. The blood pressure estimation value data related to pulse waves (and a pulse wave transit time) of a person on board is calibrated based on the blood pressure measurement value data not affected by vehicle vibration. Acquisition of an accurate blood pressure value is facilitated.

The biological sensors 10, 11 are provided in the seat 1 on which a person sits in a vehicle. Biological information is acquired and calibrated not only when a person is in the vehicle but also when the person is driving the vehicle.

When the cuff type manometer 26 is used, a blood pressure is measured with the cuff 27 being as close to a heart as possible in a resting state. Detection of an accurate blood pressure is facilitated.

The biological sensors 10, 11 provided at at least two positions in the seat are used. For example, both biological sensors 10, 11 are pulse wave sensors. Alternatively, one biological sensor 10 is an electrocardiographic sensor and the other biological sensor 11 is a pulse wave sensor. A blood pressure is estimated by known methods using pulse wave transit time.

The blood pressure estimation value data is calibrated with respect to the blood pressure measurement data. Detection of more accurate biological information is facilitated.

The blood pressure measurement value data and the blood pressure estimation value data include identification information that identifies a person. Therefore, a blood pressure of each individual is acquired.

The blood pressure measurement value data acquired by the cuff type manometer 26 is transmitted to the control device 5 provided in a vehicle through a computer network. The biological sensors 10, 11 are communicably connected to the control device 5. The blood pressure estimation value data is calibrated with reference to the blood pressure measurement value data even while the vehicle is running, for example, at a place far away from the cuff type manometer 26. An accurate blood pressure is acquired.

Example 2

Next, Example 2 will be described with reference to the drawings. For convenience of explanation, only components different from above-described Example 1 will be described.

Figure 19:
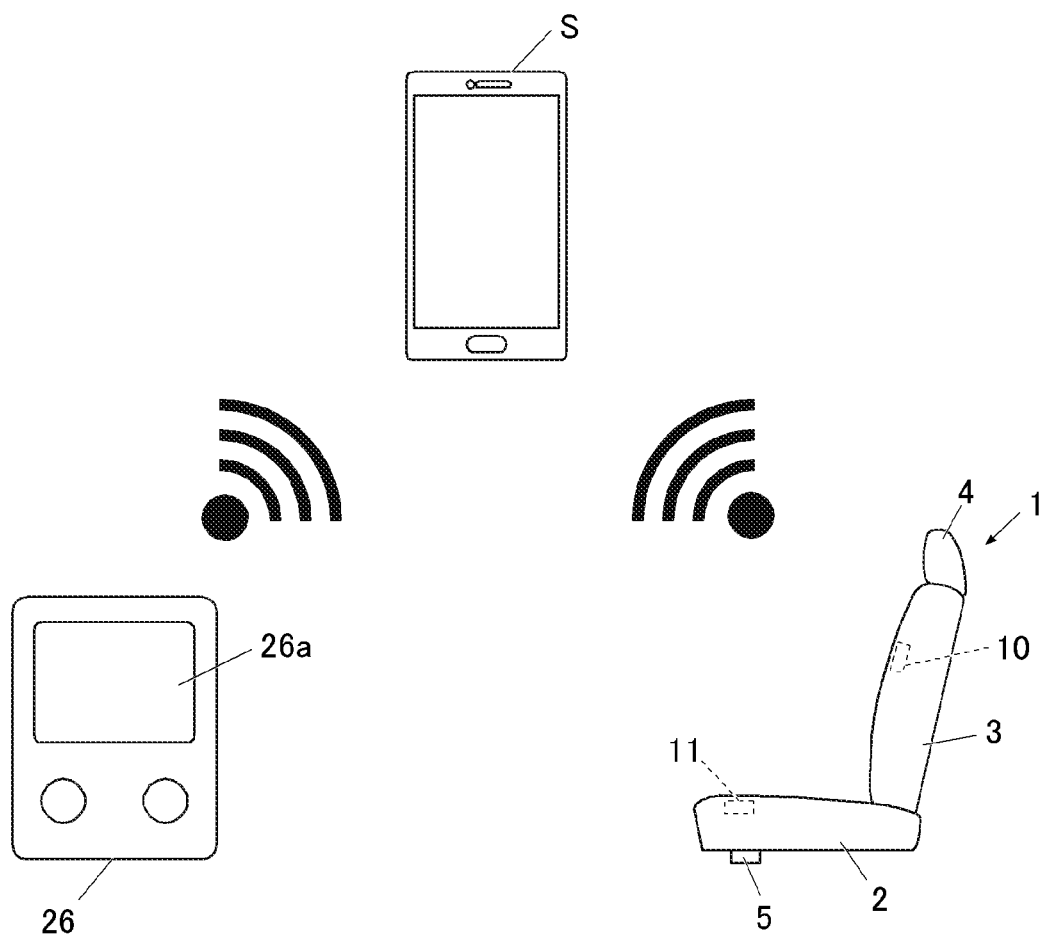
FIG. 19 describes a method of acquiring biological information using an information terminal.

In Example 2, as shown in FIG. 19, a calibrator is provided in the information terminal S. The information terminal S performs short range wireless communication with the cuff type manometer 26, which is the first measurer, and the biological sensors 10, 11 (including the control device 5), which are the second measurers.

The information terminal S is a portable information processing device such as a mobile phone or a tablet terminal. The information terminal S includes a communicator for short-range wireless communication such as Bluetooth (registered trademark). In Example 2, the information terminal S is a mobile phone.

A calibration program that makes the information terminal S function as a calibrator is stored in memory included in the information terminal S. A controller included in the information terminal S executes the calibration program.

A person to be measured by the cuff type manometer 26 and the biological sensors 10, 11 uses the information terminal S.

The cuff type manometer 26 includes a short-distance wireless communicator to transmit the blood pressure measurement value data, which is the first measurement value, to the information terminal S.

The second measurer in Example 2 is constituted by the biological sensors 10, 11 and the control device 5. Thus, the control device 5 is communicably connected to the biological sensors 10, 11, and includes the short-range wireless communicator.

A method of acquiring a blood pressure (i.e., biological information) of a seated person using the cuff type manometer 26 and the biological sensors 10, 11 will be described.

Figure 20:
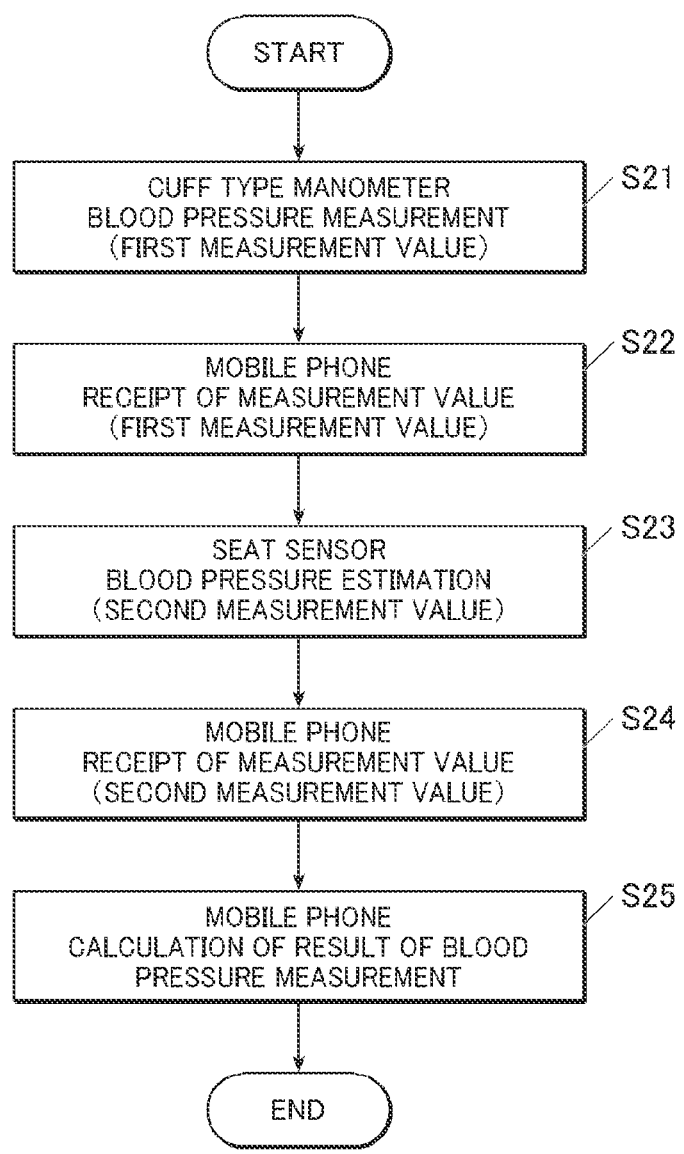
FIG. 20 is a flowchart illustrating the method of acquiring biological information using the information terminal.

As shown in FIG. 20, first, a person (seated person) measures a blood pressure with the cuff type manometer 26 outside a vehicle, in Example 2, at home (Step S21). Thereby, the blood pressure measurement value data, which is the first measurement value, is derived.

The blood pressure measurement value data is transmitted from the cuff type manometer 26 to the information terminal S using short-range wireless communication. In other words, the information terminal S receives the blood pressure measurement value data from the cuff type manometer 26 (Step S22).

A blood pressure of a seated person is estimated in a known blood pressure estimation method based on pulse wave transit time using the biological sensors 10, 11 provided in the seat 1 (Step S23). Thereby, the blood pressure estimation value data (pulse wave transit time), which is the second measurement value, is derived.

The control device 5 provided in the seat 1 transmits the blood pressure estimation value data to the information terminal S using short-range wireless communication. In other words, the information terminal S receives the blood pressure estimation value data from the control device 5 (Step S24).

The information terminal S calibrates the blood pressure estimation value data with reference to the blood pressure measurement value data, and calculates result of blood pressure measurement (Step S25). Thus, a "current" blood pressure of a person sitting on the seat 1 is derived more accurately based on the blood pressure measurement value data.

Time for the information terminal S to calibrate the blood pressure estimation value data may be:

time right after the information terminal S receives the blood pressure estimation value data from the control device 5; or any time when a person (seated person) to be measured operates a touch panel of the information terminal S.

Thus, a blood pressure of a seated person is acquired.

According to Example 2, the calibrator is provided in the information terminal S. The information terminal S performs short range wireless communication with the cuff type manometer 26, which is the first measurer, and the biological sensors 10, 11 (including the control device 5), which are the second measurers. The blood pressure measurement value data, which is the first measurement value data, is transmitted to the information terminal S in advance by short-range wireless communication. The blood pressure estimation value data is calibrated with reference to the blood pressure measurement value data even while the vehicle is running, for example, at a place far away from the cuff type manometer 26. Accurate biological information is acquired.

Example 3

Next, Example 3 will be described with reference to the drawings. For convenience of explanation, only components different from the above-described Examples 1-2 will be described.

Figure 21:
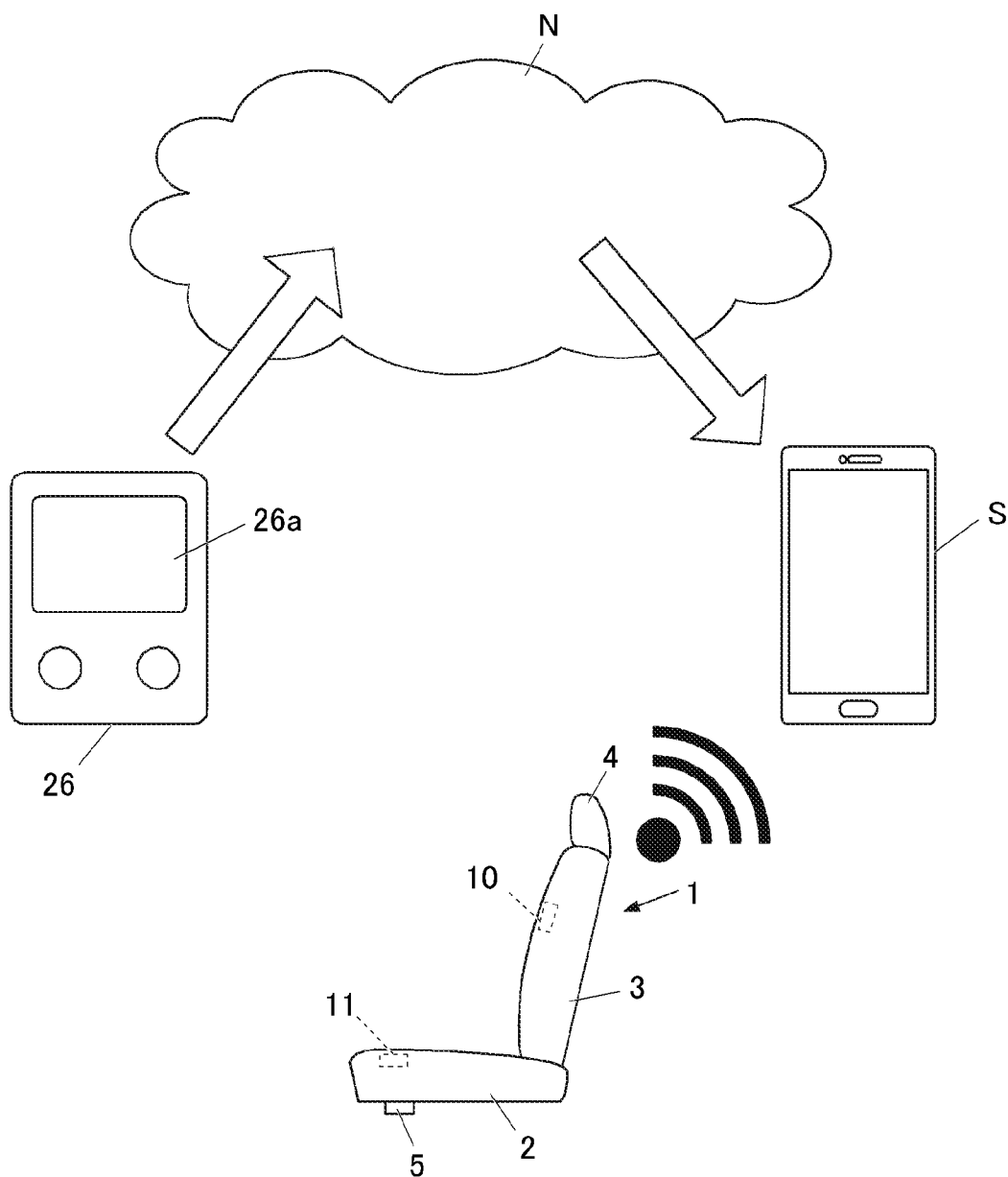
FIG. 21 illustrates a method of acquiring biological information using a computer network and an information terminal.

In Example 3, as shown in FIG. 21, a calibrator is provided in the information terminal S. The information terminal S performs short range wireless communication with biological sensors 10, 11 (including the control device 5), which are the second measurers.

The blood pressure measurement value data acquired by the cuff type manometer 26, which is the first measurer, is transmitted to the information terminal S through a computer network such as the Internet N. The blood pressure estimation value data acquired by the biological sensors 10, 11 is transmitted to the information terminal S by short-range wireless communication.

The information terminal S includes a communicator for enabling connection to the computer network such as the Internet N. The information terminal S connects to a server (not shown) that supports cloud computing via the Internet N. The information terminal S includes a communicator for short-range wireless communication such as Bluetooth (registered trademark).

The cuff-type manometer 26 includes a communicator (not shown) that transmits the blood pressure measurement value data to the outside using a computer network such as the Internet N. The cuff-type manometer 26 connects to a server (not shown) that supports cloud computing via the Internet N.

The control device 5 communicably connected to the biological sensors 10, 11 includes a short-range wireless communicator.

A method of acquiring a blood pressure (i.e., biological information) of a seated person using the cuff type manometer 26 and the biological sensors 10, 11 as described above will be described.

Figure 22:
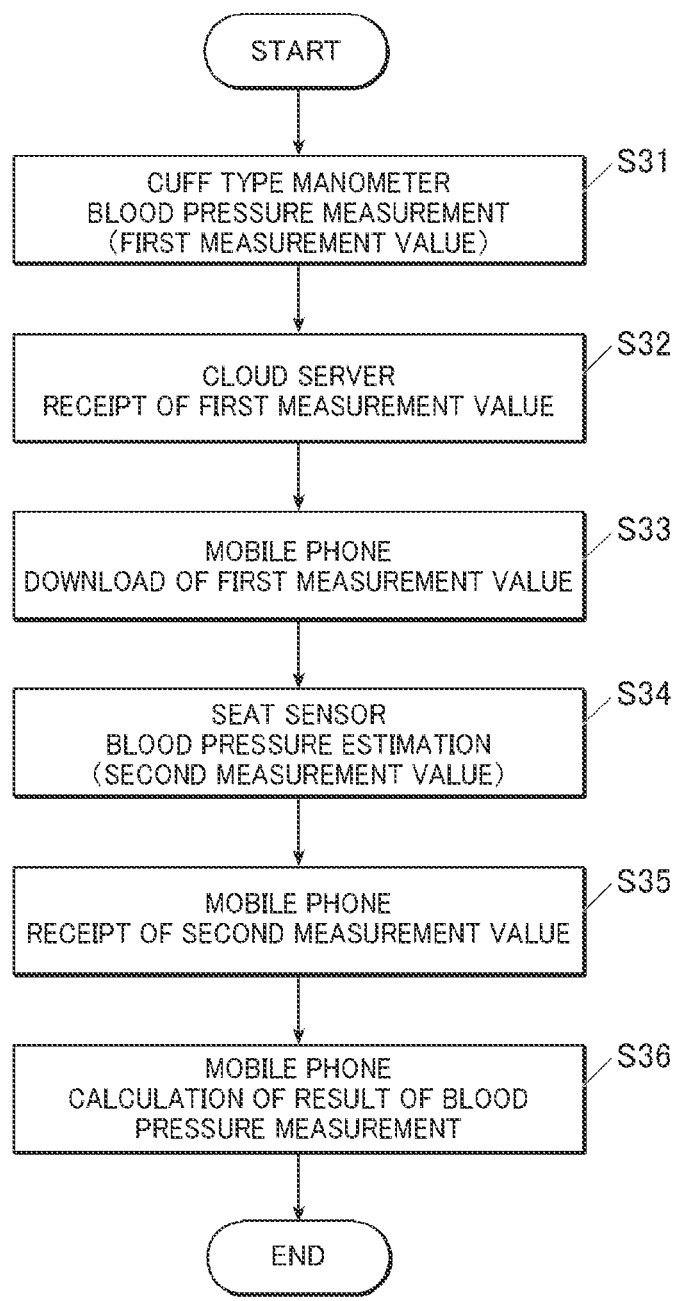
FIG. 22 is a flowchart illustrating the method of acquiring biological information using the computer network and the information terminal.

As shown in FIG. 22, first, a person (seated person) measures a blood pressure with the cuff type manometer 26 outside a vehicle, in Example 3, at home (Step S31).

Thereby, the blood pressure measurement value data, which is the first measurement value, is derived.

The communicator of the cuff-type manometer 26 transmits the blood pressure measurement value data to the server that supports cloud computing via the Internet N (Step S32).

The information terminal S downloads the blood pressure measurement value data from the server via the Internet N (Step S33).

Time for the information terminal S to download the blood pressure measurement value data may be:
- time right after the communicator of the cuff type manometer 26 transmits the blood pressure measurement value data to the server;
- time when a person sits on the seat 1; or
- time for the biological sensors 10, 11 to estimate a blood pressure after a person sits.

A blood pressure of the seated person is estimated in a known blood pressure estimation method based on pulse wave transit time with the biological sensors 10, 11 provided in the seat 1 (Step S34). Thereby, the blood pressure estimation value data (pulse wave transit time), which is the second measurement value, is derived.

The control device 5 provided in the seat 1 transmits the blood pressure estimation value data to the information terminal S using short-range wireless communication. In other words, the information terminal S receives the blood pressure estimation value data from the control device 5 (Step S35).

The information terminal S calibrates the blood pressure estimation value data with reference to the blood pressure measurement value data, and calculates result of blood pressure measurement (Step S36). Thus, a "current" blood pressure of a person sitting on the seat 1 is derived more accurately based on the blood pressure measurement value data.

Time for the information terminal S to calibrate the blood pressure estimation value data may be:
- time right after the information terminal S receives the blood pressure estimation value data from the control device 5; or
- any time when a person (seated person) to be measured operates a touch panel of the information terminal S.

Thus, a blood pressure of a seated person is acquired.

According to Example 3, the calibrator is provided in the information terminal S. The information terminal S performs short range wireless communication with the biological sensors 10, 11 (including the control device 5), which are the second measurers. The blood pressure measurement value data is transmitted to the calibrator provided in the information terminal S through the computer network. The blood pressure measurement value data is the first measurement value data acquired by the cuff type manometer 26 which is the first measurer. The blood pressure estimation value data is calibrated with reference to the blood pressure measurement value data even while the vehicle is running, for example, at a place far away from the cuff type manometer 26. Accurate biological information is acquired.

Modification 10

Hereinafter, a modification of the third embodiment will be described. The following modifications or the above modifications may be combined in possible ways.

Common reference numerals are given to elements common to the above embodiments, the above modifications, and the following modifications. Explanation is omitted or simplified.

Figure 23:
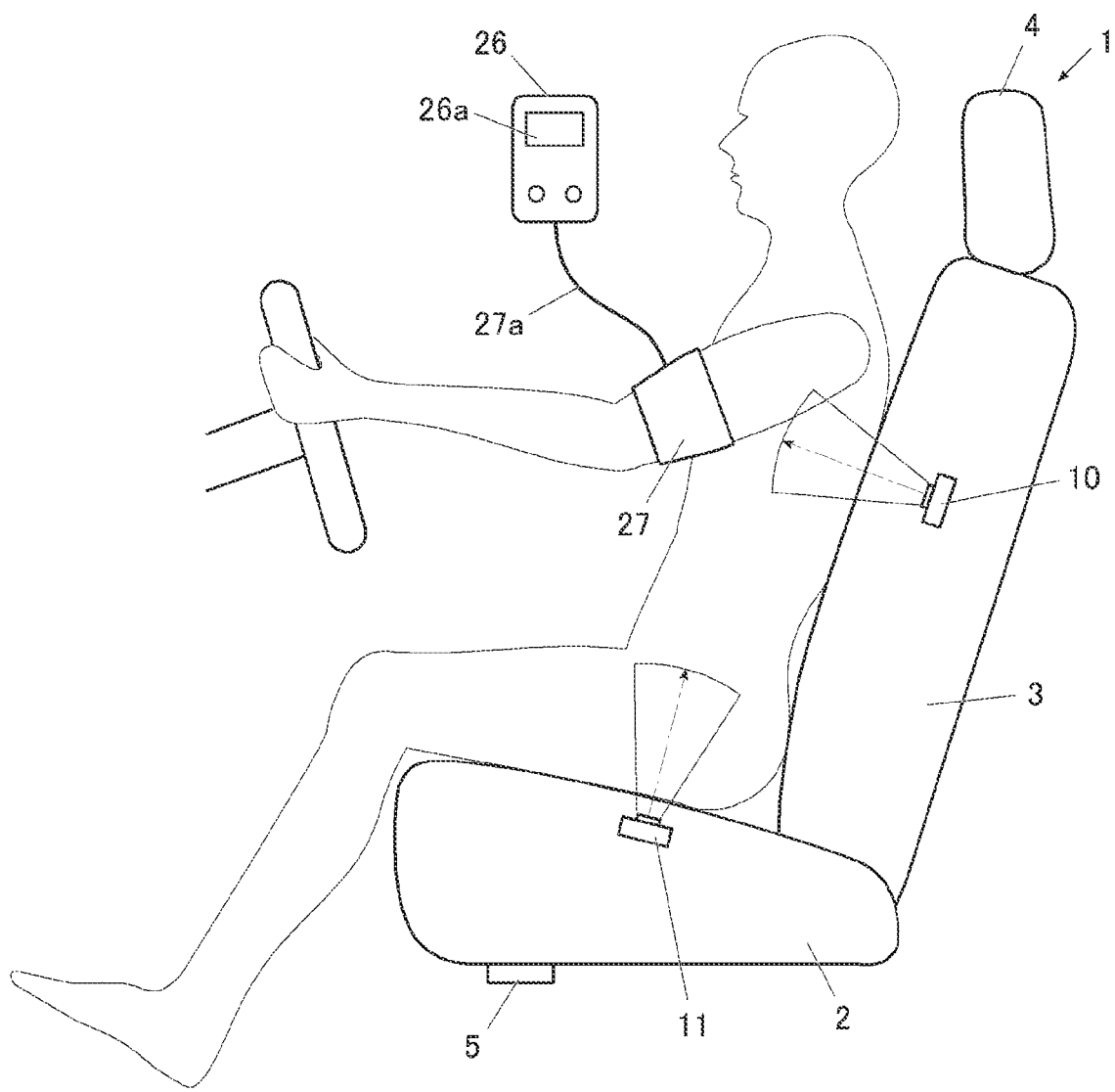
FIG. 23 shows a state in which a cuff type manometer is provided in a vehicle and biological sensors are provided at two positions on a seat.

In the modification, as shown in FIG. 23, both the first measurer and the second measurer are provided in a vehicle.

The biological sensors 10, 11 and the control device 5, which are the second measurers, are provided in the seat 1 as in the above-described embodiments.

The cuff type manometer 26, which is the first measurer, is provided at any place in the vehicle. In the modification, the cuff type manometer 26 is provided in the seat back 3 near an upper arm of a seated person or in an armrest (not shown).

In a case where the cuff type manometer 26 is provided in the seat 1, it is preferable that a body of the manometer is built into the seat 1. In that case, the seat back 3 or the armrest is provided with a storage for accommodating the cuff 27 and the air supply tube 27*a*.

In a case where the cuff type manometer 26 is provided in a vehicle and a blood pressure of a seated person is measured by the cuff type manometer 26, the blood pressure is basically measured while the vehicle is stopped. However, in a case where the vehicle travels while switching between automatic driving and manual driving, a blood pressure may be measured during automatic driving.

According to the modification, detection of more accurate biological information is facilitated as compared with a case where, for example, biological information of a person is acquired using only one of the first measurer and the second measurer. The biological information is acquired and calibrated not only when a person is in the vehicle but also when the person is driving the vehicle.

If both the first measurer and the second measurer are provided in the vehicle, it is not necessary to provide either one outside the vehicle. The system is aggregated. Efficiency of maintenance and the like is improved.

Fourth Embodiment

Next, a fourth embodiment of the present invention will be described with reference to the drawings. For convenience of explanation, the same reference numerals are given to components common to the first to third embodiments and the fourth embodiment. Components different from the first to third embodiments will be mainly described. Duplicate explanations are given when necessary.

In conventionally known technique, for example, technique described in JP 2018-097457A, information on accidents which scare or surprise a driver of a vehicle (hereinafter referred to as scary/surprising accidents) are accumulated in a database. The information accumulated in the database is provided to vehicles as driving support information.

Conventionally, acceleration sensors are provided in some vehicles. A scary/surprising accident is identified based on acceleration detected by the acceleration sensor. A case where a vehicle suddenly moves due to hard braking or sudden steering is identified as a scary/surprising accident.

However, it is an occupant in a vehicle who is scared or surprised. There was a request to improve reliability of accumulated data by using biological information of an occupant to identify scary/surprising accidents.

Therefore, the fourth problem is to improve reliability of data accumulated as the driving support information by acquiring biological information of an occupant in scary/surprising accidents.

To solve such a problem, the thirty-first invention shown in the embodiment is a driving support information accumulation system, including:
- a biological information acquisition unit that acquires biological information of a person when a scary/surprising accident happens;

a scary/surprising accident information acquisition unit that acquires scary/surprising accident information related to a situation where the scary/surprising accident happens;
an association unit that associates the biological information with the scary/surprising accident information; and
a database which collects the biological information and the scary/surprising accident information associated by the association unit and which accumulates the biological information and the scary/surprising accident information as driving support information.

The thirty-second invention shown in the embodiment is the driving support information accumulation system according to the thirty-first invention, wherein the scary/surprising accident information includes position information, time information, and driving operation information of a vehicle in the scary/surprising accident.

The thirty-third invention shown in the embodiment is the driving support information accumulation system according to the thirty-first or thirty-second invention, wherein the biological information acquisition unit includes a biological sensor provided in a seat of the vehicle.

The thirty-fourth invention shown in the embodiment is the driving support information accumulation system according to the thirty-third invention, further including:
a first measurer and a second measurer each of which acquires the biological information of the person; and
a calibrator that receives:
data of first measurement value of the biological information measured by the first measurer; and
data of second measurement value of the biological information measured by the second measurer,
wherein
the calibrator calibrates the second measurement value with reference to the first measurement value,
the first measurer is outside the vehicle, and
the second measurer is the biological sensor provided in the seat.

The thirty-fifth invention shown in the embodiment is the driving support information accumulation system according to the thirty-fourth invention, wherein
the first measurer is a manometer including a cuff that winds around a limb of the person, and
the second measurer is biological sensors provided at at least two positions in the seat.

The thirty-sixth invention shown in the embodiment is a driving support information accumulation system according to any one of the thirty-first to thirty-fifth inventions, further including:
a learning unit that learns characteristics of the driving support information accumulated in the database.

The thirty-seventh invention shown in the embodiment is a driving support information accumulation system according to any one of the thirty-first to thirty-sixth inventions, further including:
a server that provides a user with service based on the driving support information accumulated in the database.

The thirty-eighth invention shown in the embodiment is the driving support information accumulation system according to the thirty-seventh invention, wherein
the server reflects the scary/surprising accident information in map information to create a scary/surprising accident map, and
the server provides a user with the scary/surprising accident map.

The thirty-ninth invention shown in the embodiment is the driving support information accumulation system according to the thirty-seventh invention, wherein
the server provides the user with a scary/surprising accident rate of each user, and
the scary/surprising accident rate is a ratio of scary/surprising accidents to a number of times and/or a time length of driving.

The fortieth invention shown in the embodiment is the driving support information accumulation system according to any one of the thirty-first to thirty-ninth inventions, wherein the driving support information includes identification information that identifies the person.

According to the thirty-first invention, biological information in a scary/surprising accident and the scary/surprising accident information are associated and accumulated in the database. Therefore, when the accumulated driving support information is utilized, the driving support information includes the biological information and a situation when the scary/surprising accident happens.

Reliability of the data is higher than that of, for example:
a case where occurrence of a scary/surprising accident is identified based solely on biological information; or
a case where occurrence of a scary/surprising accident is identified based solely on movement of a vehicle.

According to the thirty-second invention, the scary/surprising accident information includes position information, time information, and driving operation information of the vehicle in a scary/surprising accident. Therefore, it is easy to recall a situation of the scary/surprising accident.

According to the thirty-third invention, the biological information acquisition unit includes the biological sensor provided in the seat of the vehicle. Therefore, biological information of a person sitting on the seat can be easily acquired and used as the driving support information. Biological information can be acquired not only when a person is in the vehicle but also when the person is driving the vehicle.

According to the thirty-fourth invention, in a case where the first measurer is not provided in the vehicle, the first measurer does not receive vibration from the vehicle. Therefore, the second measurement value related to biological information of a person on board is calibrated with reference to the first measurement value, which is not affected by vehicle vibration. Detection of accurate biological information is facilitated.

According to the thirty-fifth invention, the first measurer is a manometer including a cuff that winds around a limb of the person. Measurement is made with the cuff being as close to a heart as possible in a resting state. Detection of an accurate blood pressure is facilitated.

The second measurer is the biological sensors provided at at least two positions in the seat. For example, both biological sensors are pulse wave sensors. Alternatively, one biological sensor is an electrocardiograph and the other biological sensor is a pulse wave sensor. A blood pressure is estimated by known methods using pulse wave transit time.

The second measurement value is then calibrated with reference to the first measurement value. Detection of more accurate biological information is facilitated.

The thirty-sixth invention further includes the learning unit that learns characteristics of the driving support information accumulated in the database. The learning unit continues to learn the characteristics of driving support information. It improves accuracy of detection of biological information. For example, a cause of fluctuation in biological information which was difficult to be accurately identified can be determined to be a scary/surprising accident.

The learning unit continues to learn characteristics of the driving support information so that a scary/surprising accident can be predicted based on characteristics and tendencies of each user.

The thirty-seventh invention further includes the server that provides service to a user based on the driving support information accumulated in the database. The server provides a user with high quality service which is based on the driving support information with improved reliability as data.

According to the thirty-eighth invention, the server reflects the scary/surprising accident information in map information. The server creates a scary/surprising accident map and provides it to the user. It is expected that the created scary/surprising accident map will be used in various fields. Widespread use of the scary/surprising accident map contributes to reduction of the number of scary/surprising accidents.

According to the thirty-ninth invention, the server provides a user with a scary/surprising accident rate of each user. The scary/surprising accident rate is a ratio of scary/surprising accidents to the number of times and/or a time length of driving. It calls a user's attention. It contributes to reduction of the number of scary/surprising accidents for each user.

According to the fortieth invention, the driving support information includes identification information that identifies a person. Biological information of each user is acquired. Biological information and the scary/surprising accident information are easily associated.

Embodiments will be described in more detail.

Figure 24:
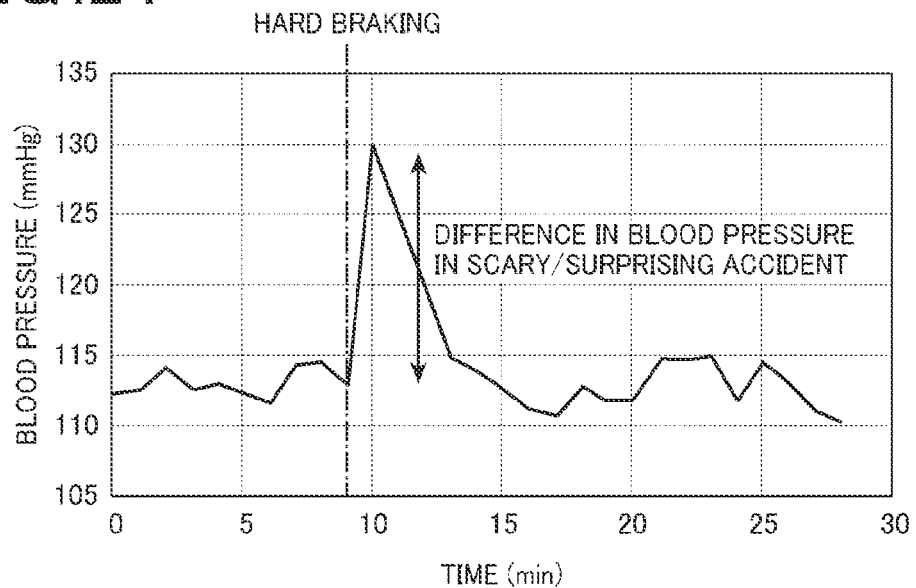
FIG. 24 is a graph showing correlation between occurrence of a scary/surprising accident and biological information (blood pressure).

As is conventionally known, when a so-called scary/surprising accident (scary accident or surprising accident) happens while a vehicle is running, blood pressure fluctuates as shown in FIG. 24.

At the time of the scary/surprising accident, fluctuation may occur not only in blood pressure but also in biological information such as heartbeats, a heart rate (including electrical activity of a heart which is represented by an electrocardiogram), sweating, eye or pupil movement, and body movement. Such fluctuation in biological information may occur not only right after the scary/surprising accident but also a certain time after the scary/surprising accident. At those times, as is conventionally known, a further scary/surprising accident is likely to occur.

Figure 25:
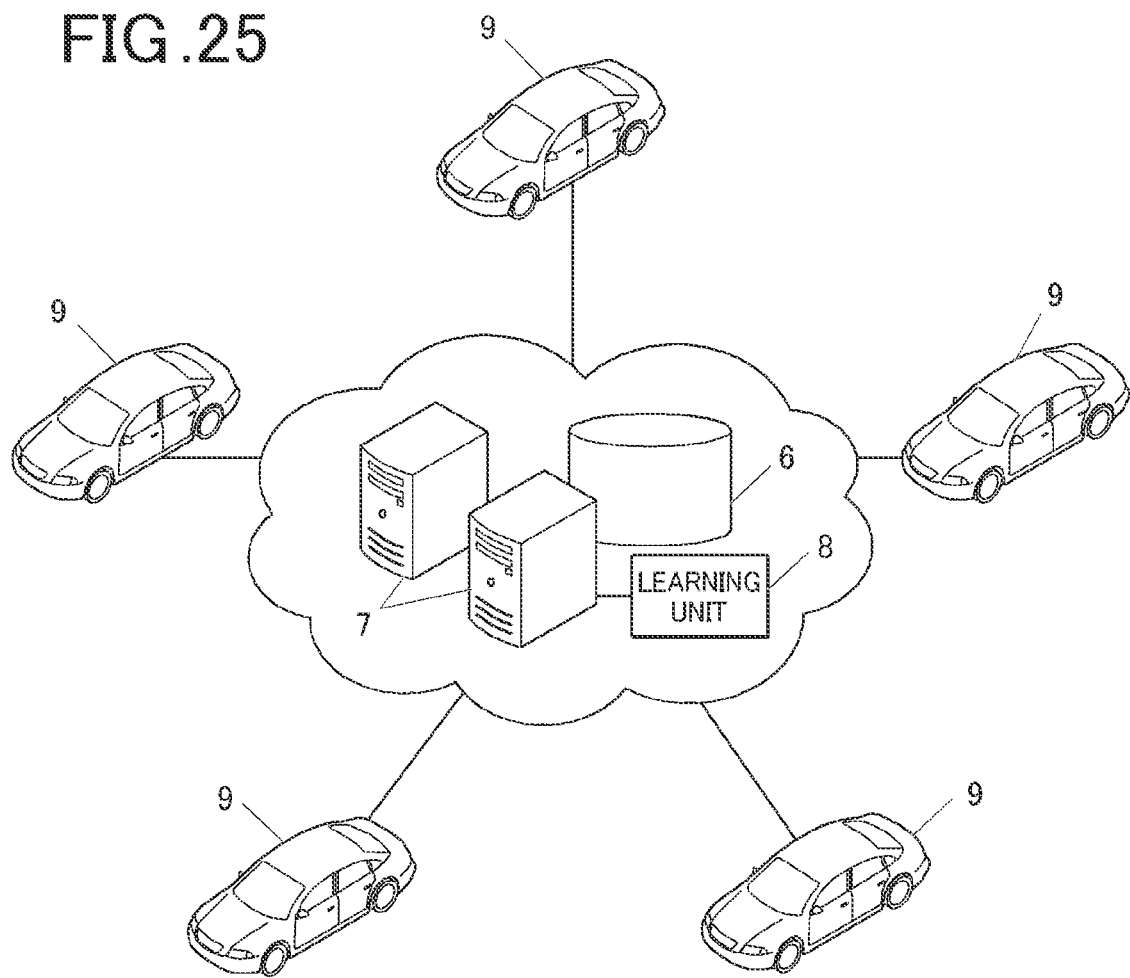
FIG. 25 describes an outline of a driving support information accumulation system.

Therefore, in the embodiment, as shown in FIGS. 15 and 25, the biological sensors 10, 11 provided in the seat 1 of a vehicle 9 measure biological information. The biological information is transmitted to a server 6 via a computer network N such as the Internet. The biological information is accumulated in a database 7 provided in the server 6. The biological information accumulated in the database 7 is provided to a user from the server 6 as the driving support information.

Users include various people, for example, an owner and occupants of the vehicle 9, and a company that wants to provide service utilizing the driving support information.

The seat 1 shown in FIG. 15 is provided in a vehicle such as a car. The vehicle may travel while being driven only manually. Alternatively, the vehicle may travel while switching between automatic driving and manual driving.

The seat 1 includes:
a seat cushion 2 that supports buttocks and thighs of a person;
a seat back 3 which serves as a backrest and which has a lower end supported by the seat cushion 2; and
a headrest 4 provided on the seat back 3 to support a head of a person.

The seat cushion 2 mainly includes:
a seat cushion frame that is a skeleton;
a cushion pad provided on the seat cushion frame; and
a cover that covers the seat cushion frame and the cushion pad.

The seat back 3 mainly includes:
a seat back frame that is a skeleton;
a cushion pad provided on the seat back frame; and
a cover that covers the seat back frame and the cushion pad.

The seat 1 is provided with the biological sensors 10, 11 as a means (biological information acquisition unit) for recognizing health condition of a seated person (living body). More specifically, each of the biological sensors 10, 11 in the embodiment detects pulse waves as biological information from a blood flow at a position opposite to a skin surface of the seated person.

In the embodiment, a position of one biological sensor 10 corresponds to a position of a heart (thoracic aorta) of a seated person. It is provided in the cushion pad of the seat back 3 on a side of the seated person and on an inner side of the cover. A position of the other biological sensor 11 corresponds to a position of buttocks (center of left and right ischia) or thighs of the seated person. The biological sensor 11 is provided in the seat cushion 2 on an upper side of the cushion pad and on an inner side of the cover.

The biological sensor 10 corresponding to the position of the heart of the seated person may be an electrocardiographic sensor that takes an electrocardiogram (including electrical activity of a heart which is represented by an electrocardiogram) of the seated person.

The biological sensors 10, 11 that detect pulse waves are, for example:
photoelectric pulse wave sensors that measure pulse waves of a seated person using light;
piezoelectric pulse wave sensors that measure pulse waves of a seated person by measuring pressure waves on a body surface of a seated person; or
electromagnetic wave type pulse wave sensors that measure pulse waves of a seated person using electromagnetic waves.

In the embodiment, any of these types of pulse wave sensors may be adopted. Those types of pulse wave sensors may be used in combination.

The seat 1 is provided with the control device 5 (biological information acquisition unit). The control device 5 is connected to each of the biological sensors 10, 11 by a harness or the like so as to be capable of data communication. The control device 5 in the embodiment is provided at a lower part of the seat 1. Thus, the control device 5 is provided in a vehicle.

The control device 5 is also called a so-called ECU (electronic controller). The control device 5 functions as a blood pressure estimation unit that estimates a blood pressure of a seated person from pulse waves (electrocardiogram) acquired by the biological sensors 10, 11. Memory (not shown) in the control device 5 stores a blood pressure estimation program. The control device 5 calculates and derives data related to an estimated value of a blood pressure of a seated person (blood pressure estimation data) based on the blood pressure estimation program.

More specifically, a blood pressure is estimated using a known blood pressure estimation method based on pulse wave transit time on the basis of:
- a distance between two points where the biological sensors 10, 11 are placed; and
- a difference in time of sensing pulse waves between the two points where the biological sensors 10, 11 are placed.

The blood pressure estimation program is created based on the blood pressure estimation methods, and is executed by the control device 5.

In other words, as shown in FIG. 24, the biological sensors 10, 11 are placed at at least two different positions in the seat 1. Thereby, pulse wave data is detected from the at least two positions on a body of a seated person. Accuracy of calculation of health condition of a seated person by estimating a blood pressure from detected pulse wave data is improved as compared with a case where only one biological sensor is used.

The control device 5 further includes a communicator for connecting to a computer network such as the Internet N. The control device 5 connects to the server 6 via the computer network N. The communicator transmits acquired biological information to the server 6.

The biological sensors 10, 11 continuously or periodically acquire biological information while a vehicle is running. The control device 5 stores a threshold value for determining occurrence of a scary/surprising accident. If fluctuation of biological information exceeds the threshold value, the control device 5 determines that a scary/surprising accident happens. The control device 5 transmits the biological information in the scary/surprising accident and before and after the accident to the server 6.

The biological information includes identification information that identifies an individual. Means for identifying an individual is not particularly limited.

For example, an individual is identified by:
- transmission of ID (identification information) of a seated person to the control device 5;
- input of information by a seated person;
- use of a seating sensor that measures a weight; or
- use of other personal authentication means.

Equipment and functions necessary for identifying an individual are provided in a vehicle.

The biological information includes time information of occurrence of a scary/surprising accident (time of a scary/surprising accident and a driving time). A timer built into the control device 5 acquires the time information.

Thus, biological information accumulated in the database 7 is associated with the identification information. The biological information can be fed back to a user.

Biological information is associated with the scary/surprising accident information including:
- position information (longitude and latitude) of a scary/surprising accident;
- time information (time of a scary/surprising accident and a driving time); and
- driving operation information (hard braking, sudden steering, driving speed, etc.) of a vehicle in the scary/surprising accident.

The scary/surprising accident information may include video data of a drive recorder in the scary/surprising accident.

The position information acquisition unit is, for example, a GPS (global positioning system). A radio wave receiver is provided in the vehicle 9. The receiver is connected to the control device 5 so as to be capable of data communication. The control device 5 can acquire the position information of a scary/surprising accident.

A timer built into the control device 5 acquires the time information.

Acceleration sensors and speedometers provided in the vehicle 9 acquire the driving operation information. The acceleration sensor and the speedometer are connected to the control device 5 so as to be capable of data communication. The control device 5 can acquire the driving operation information of a scary/surprising accident.

If all the data during driving of the vehicle were transmitted to the server 6, the data would be heavy. Therefore, these various types of information associated with biological information are transmitted to the server 6 as fragmentary data for a predetermined number of seconds before and after a scary/surprising accident.

In the embodiment, the control device 5 performs processing of associating biological information with the scary/surprising accident information. Thus, the control device 5 functions as an association unit. The memory stores a program for associating biological information with the scary/surprising accident information based on the time information common to them. In a case where the scary/surprising accident information includes the identification information, the server 6 may perform the processing of associating biological information with the scary/surprising accident information based on the identification information.

Biological information and the scary/surprising accident information transmitted to the server 6 are accumulated in the database 7 as the driving support information.

The driving support information accumulated in the database 7 includes biological information, the identification information, the position information, the time information, and the driving operation information in a scary/surprising accident. Therefore, the driving support information indicates to whom and in what kind of situation a scary/surprising accident happen.

For example, a scary/surprising accident happens in a situation where a user "drives at 50 km/h for 4 hours" at a point of "longitude X and latitude Y (position information: for example, an intersection)" at "23:37 on Dec. 10, 2018, Japan time (time information)". The scary/surprising accident information of such a scary/surprising accident reminds people of a situation where a user "drives at a speed within a legal speed range for a long time at an intersection at a late hour". In such a situation, the late hour and the long driving time are supposed to have caused the scary/surprising accident. The intersection is supposed to be a secondary factor. If there are many scary/surprising accidents happening at the same intersection regardless of day or night, the intersection or a structure of the intersection is sometimes supposed to have caused the scary/surprising accident.

For example, a scary/surprising accident happens in a situation where a user "drives at 31 km/h for 0.5 hours" at a point of "longitude X and latitude Y (position information: for example, a school route of an elementary school)" at "15:13 on Dec. 10, 2018, Japan time (time information)". The scary/surprising accident information of such a scary/surprising accident reminds people of a situation where a user "drives at an overspeed for a short time in a school route (school zone) when elementary school students return home". In such a situation, the overspeed and the hour when elementary school students return home are supposed to have caused the scary/surprising accident. The length of driving time is supposed to be a secondary factor.

In the database 7, information may be classified according to kinds and be accumulated. The driving support information may be classified according to situations and accumulated. Such driving support information classified according to situations contributes to analysis of tendency of scary/surprising accidents.

In the embodiment, blood pressure is measured and acquired as biological information. Alternatively, the above-mentioned other sensors, various devices, and the like for acquiring biological information may be used. Biological information of several kinds may be acquired and transmitted to the server 6.

Although not shown in the drawings, more specifically, for example, to detect a heart sound, a heart sound sensor that acquires a heart sound signal is used. To detect a heart rate, a heart rate sensor that detects the heart rate is used. To detect sweating or eye/pupil movement, for example, a camera installed in a vehicle is used. To detect body movement, for example, a camera or a body pressure sensor provided in the seat 1 is used.

Sensors and devices for acquiring biological information are communicably connected to the control device 5. The control device 5 converts data of detected biological information (signal).

The server 6 collects biological information and the scary/surprising accident information. The server 6 provides a user with the driving support information configured based on the collected biological information and the scary/surprising accident information as service.

The server 6 executes processing according to requests from:
  the control device 5 provided in the seat 1 of the vehicle 9; and
  other client devices (for example, a computer and information terminals such as a mobile phone and a tablet terminal) connected via the computer network N.

The server 6 includes:
  the database 7 where the driving support information is accumulated; and
  a learning unit 8 that learns the driving support information accumulated in the database 7.

The server 6 includes functions (controller, memory, communicator, input, output, etc.) required for service provided to users.

In addition to the driving support information, the database 7 stores information necessary for the service provided to the user, such as information related to a scary/surprising accident rate. The scary/surprising accident rate is a ratio of scary/surprising accidents to a number of times and/or a time length of driving.

The driving support information includes:
  "personal data" which is classified according to users and accumulated; and
  "common data" which is collected from all the users and accumulated without being classified according to users.

The learning unit 8 learns biological information and the scary/surprising accident information (that is, the driving support information) accumulated in the database 7.

The learning unit 8 is executed by a program including:
  a known artificial intelligence; or
  an artificial intelligence obtained by improving the known artificial intelligence.

Result of learning by the learning unit 8 is utilized in service provided to users.

More specifically, the learning unit 8 continues to learn about biological information and the scary/surprising accident information in scary/surprising accidents. Thereby, accuracy of detecting biological information is improved. For example, sometimes it is not possible to accurately determine whether fluctuation of biological information acquired by the biological sensors 10, 11 is caused by a scary/surprising accident. Even in that case, data accumulation and learning are performed. Thereby, for example, it becomes clear that a place where biological information fluctuates is a place where a scary/surprising accident is likely to happen.

In another example, it is determined that a cause of fluctuation of biological information that could not be accurately identified is a scary/surprising accident in:
  a case where the biological information fluctuates at night; or
  a case where the biological information of not only one user but several users fluctuates.

The learning unit 8 accumulates and learns such data.

Since accuracy of detecting biological information for which a cause could not be accurately identified is improved, a threshold value that can be applied to many users can be set. For example, if a fluctuation value of biological information at a certain point exceeds the threshold value, it is determined that the fluctuation is caused by a scary/surprising accident.

These examples are realized by using common data as well as personal data.

The learning unit 8 continues to learn only personal data. Thereby, the driving support information suitable for each user can be provided. Each user has characteristics and tendencies in driving the vehicle 9. For example, some people are not good at turning left (if one is driving on the right side, turning right), where difference between tracks followed by front and rear inner wheels when turning needs to be fully considered. Some people often start suddenly or brake suddenly. Those characteristics and tendencies sometimes cause a scary/surprising accident. Even in that case, data accumulation and learning are performed. Thereby, a scary/surprising accident can be predicted based on characteristics and tendencies of each user.

Figure 26:
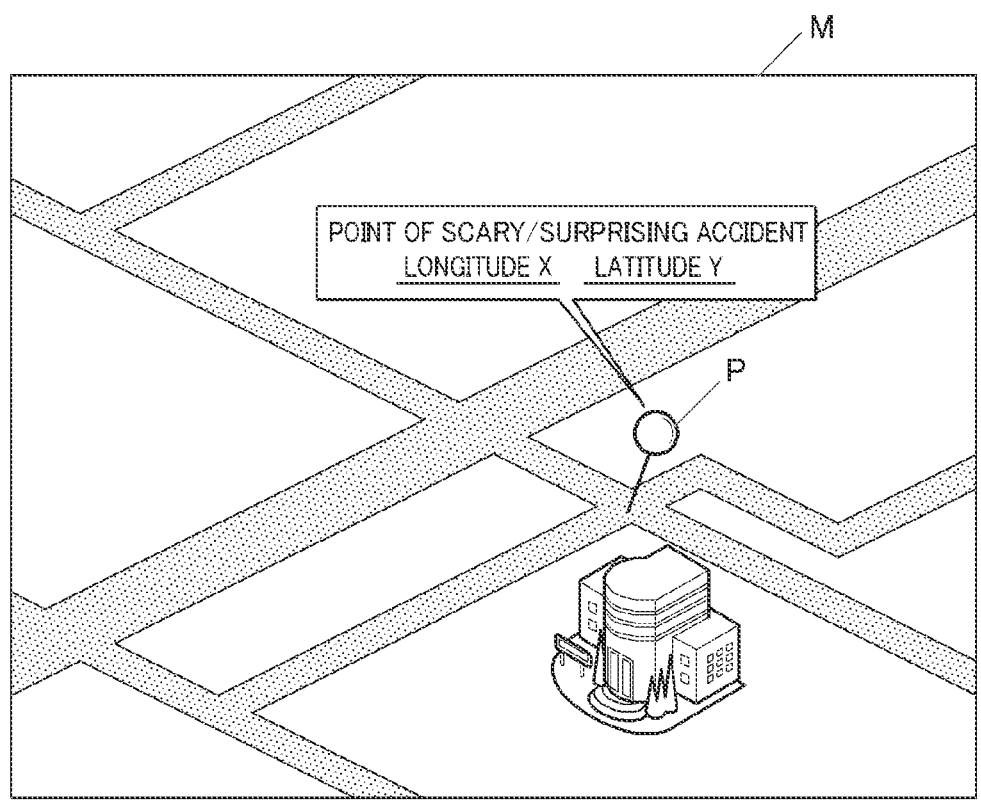
FIG. 26 shows an example of a scary/surprising accident map.

Service provided to users by the server 6 is, for example, as shown in FIG. 26, service of creating a scary/surprising accident map by reflecting the scary/surprising accident information (or the driving support information associated with biological information) in a map information M.

The map creation service is a service that reflects the scary/surprising accident information in the map information M and transmits map information data to a user via the computer network N. In FIG. 26, a pin P indicates a position of the scary/surprising accident information.

After the map information data is transmitted to the control device 5 of the vehicle 9, the service may use a display or a voice output (or other notification unit such as a light emitter) of a car navigation system in the vehicle. In a case where the car navigation system includes a communicator, the map information data may be transmitted directly to the car navigation system.

Alternatively, the map information data may be programmed and installed in a car navigation system or various other information terminals (such as a computer, a mobile phone, and a tablet terminal). In that case, it is necessary to update the data (version upgrade) regularly.

In the map creation service, common data is usually utilized to provide highly versatile map information data to users. Instead, personal data may be utilized to provide the map information data suitable for each user.

Such a map creation service has a function of announcing and alerting a user that it is a scary/surprising accident point (or close to a scary/surprising accident point) when approaching the scary/surprising accident point (or a point close to it).

In a case where the map creation service is based on the map information data utilizing personal data, the service has a function to announce and call attention which is suitable for each user.

An example of service that accompanies the map creation service as described above is service of utilization for infrastructure development. At a point where a scary/surprising accident often happens, for example, improvement of a road structure, or amendment to a law regarding change in the maximum speed is required. Therefore, such utilization service for infrastructure development is mainly provided to administrative agencies (such as Ministry of Land, Infrastructure, Transport and Tourism, Ministry of Health, Labor and Welfare, Ministry of Education, Culture, Sports, Science and Technology, Metropolitan Police unit, and National Police Agency). Utilization service may also be provided to common persons, companies and organizations.

Another example of service provided to users by the server 6 is service that provides a scary/surprising accident rate of each user. As described above, the scary/surprising accident rate is a ratio of scary/surprising accidents to a number of times and/or a time length of driving. It is desirable to clarify whether it is a scary/surprising accident caused by characteristics and tendencies of a user's driving or a scary/surprising accident caused by other external factors.

To provide a user with information related to a scary/surprising accident rate, the information is provided when the scary/surprising accident rate reaches a certain level (threshold value) or higher. Providing the information about a scary/surprising accident rate to a user with a high scary/surprising accident rate serves as a caution to the user. The learning unit 8 may learn the threshold setting in that case.

Such service of providing information of a scary/surprising accident rate is basically for respective users. The service is not limited to this. The service may be incorporated or utilized in other service provided to each user.

Service provided by the server 6 is not limited to those shown above.

According to the embodiment, biological information in a scary/surprising accident and the scary/surprising accident information are associated with each other and then accumulated in the database 7. When the accumulated driving support information is utilized, the driving support information includes biological information and a situation in a scary/surprising accident.

Reliability of the data is higher than that of, for example:
a case where occurrence of a scary/surprising accident is determined based only on biological information; or
a case where occurrence of a scary/surprising accident is determined based only on movement of the vehicle 9.

The scary/surprising accident information includes position information, time information, and driving operation information of a vehicle in a scary/surprising accident. Therefore, it is easy to recall a situation of the scary/surprising accident.

The biological information acquisition unit includes the biological sensors 10, 11 provided in the seat 1 of the vehicle 9. Biological information of a person seated on the seat 1 is easily acquired and easily utilized as the driving support information. Biological information can be acquired not only when a person is in the vehicle but also when the person is driving the vehicle.

A learning unit 8 that learns characteristics of the driving support information accumulated in the database 7 is further included. The learning unit 8 continues to learn characteristics of the driving support information. It improves accuracy of detection of biological information. For example, a cause of fluctuation in biological information which was difficult to be accurately identified can be determined to be a scary/surprising accident.

The learning unit 8 continues to learn characteristics of the driving support information so that a scary/surprising accident can be predicted based on characteristics and tendencies of each user.

The server 6 that provides service based on the driving support information accumulated in the database 7 to a user is further included. The server 6 provides a user with high quality service which is based on the driving support information with improved reliability as data.

The server 6 reflects the scary/surprising accident information in the map information M to create the scary/surprising accident map. The server 6 provides a user with the scary/surprising accident map. It is expected that the created scary/surprising accident map will be used in various fields. Widespread use of the scary/surprising accident map contributes to reduction of the number of scary/surprising accidents.

The server 6 provides a user with the scary/surprising accident rate, which is a ratio of scary/surprising accidents to the number of times and/or a time length of driving. Thus, the server 6 calls the user's attention. It contributes to reduction of the number of scary/surprising accidents for each user.

The driving support information includes identification information that identifies a person. Therefore, biological information of each user can be acquired. Biological information and the scary/surprising accident information are easily associated.

EXAMPLES

Examples of the biological information acquisition unit according to the embodiment will be described with reference to the drawings.

Common reference numerals are given to elements common to the above embodiments and following Examples.

Example 4

In this Example, first, configuration related to the biological sensors 10, 11 and the control device 5 is adopted. They are the second measurers in this Example. The blood pressure estimation value data derived by the second measurer is the second measurement value.

In the blood pressure estimation method based on pulse wave transit time in the above embodiment, a blood pressure is estimated using the biological sensors 10, 11.

As shown by experimental data of FIGS. 16A to 16B, according to the method, difference among individuals tends to be large. Data of one person tends to vary. Further, data tends to be affected by vibration of a vehicle.

Figure 27:
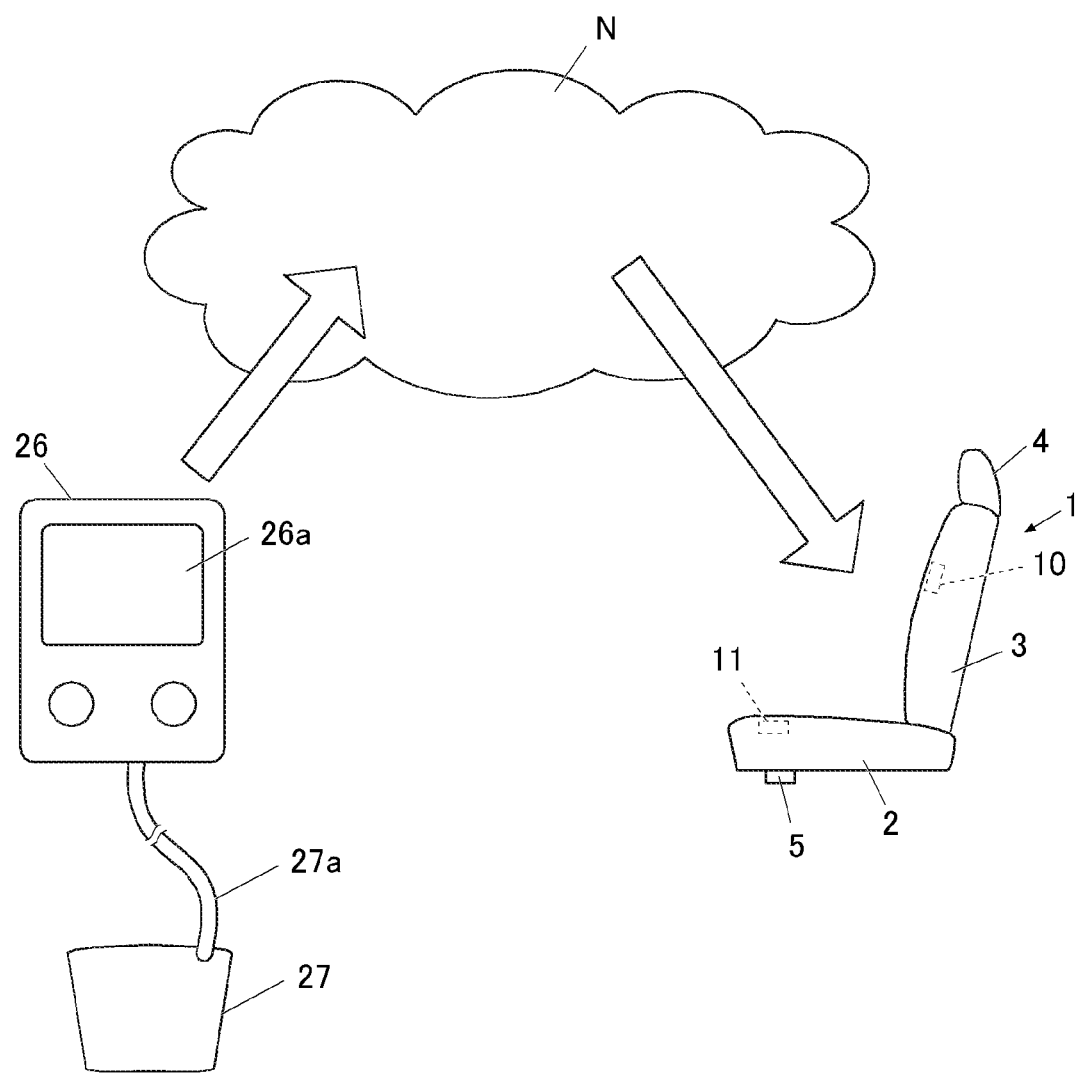
FIG. 27 describes a method of acquiring biological information using a computer network.

In this Example, a blood pressure can be easily derived by using the blood pressure estimation method based on pulse wave transit time even while a person is in the vehicle 9. To achieve this, as shown in FIG. 27, a blood pressure is measured several times in advance by the manometer 26 including the cuff 27 that can be worn on a limb of a person (hereafter called the cuff type manometer 26). The control device 5 uses blood pressure measurement value data measured by the manometer as a reference. The control device 5 calibrates the blood pressure estimation value data estimated in the blood pressure estimation method based on pulse wave transit time.

Thus, in this Example, the cuff type manometer 26 is the first measurer. The blood pressure measurement value data acquired by the cuff type manometer 26 is the first measurement value.

The control device 5 also functions as a calibrator that calibrates the blood pressure estimation value data (second measurement value) with reference to the blood pressure measurement value data (first measurement value).

More specifically, memory of the control device 5 stores a calibration program for realizing a function as the calibrator. The control device 5 calibrates the blood pressure estimation value data with reference to the blood pressure measurement value data based on the calibration program.

Such a calibration program makes the control device 5, which is a computer, function as the calibrator. The calibrator calibrates the data of the second measurement value with reference to the data of the first measurement value. The first measurement value relates to biological information of a person which is measured by the first measurer that acquires the biological information. The second measurement value relates to biological information of a person which is measured by the second measurer that acquires the biological information.

The blood pressure estimation value data includes pulse waves transit time (PWTT). As described above, the blood pressure estimation value data includes identification information that identifies an individual.

The cuff type manometer 26 adopts a method of indirect measurement (also called an indirect method, non-invasive type, or non-operative type). In the embodiment, the cuff type manometer 26 is an automatic manometer capable of mechanical measurement.

A body of the cuff type manometer 26 includes at least:
 the display 26a that displays a blood pressure;
 a pump (not shown) that sends air to a cuff 27; and
 a communicator (not shown) that transmits data to the outside.

The communicator uses the computer network N such as the Internet to transmit the blood pressure measurement value data to the outside.

The communicator in the embodiment transmits blood pressure measurement value data to the server 6 via the Internet. The server 6 to which the blood pressure measurement value data is transmitted may be replaced with a server device other than the server 6 in the above embodiments.

The blood pressure measurement value data measured by the cuff type manometer 26 includes identification information that identifies an individual. Means for identifying an individual is not particularly limited.

For example, an individual is identified by:
 transmitting ID (identification information) to the cuff type manometer 26;
 reading ID constituted by barcode or the like;
 entering information oneself; or
 use of other personal authentication means.

The cuff type manometer 26 or a peripheral device has a function necessary for identifying an individual.

The cuff 27 is a compression band that winds around a limb of a person. The cuff 27 is inflated by pumping air from the pump of the manometer body. An acoustic sensor such as a microphone built into the cuff 27 detects a blood pressure.

The manometer body and the cuff 27 are connected by:
 a connection line that transmits sensing information from the acoustic sensor to the manometer body; and
 the air supply tube 27a that sends air from the pump of the manometer body to the cuff 27.

In this Example, the cuff type manometer 26 is outside a vehicle. Specifically, the cuff type manometer 26 is at a home of a person sitting on the seat 1. The location is not limited to this. The cuff type manometer 26 may be placed in a medical institution such as a hospital, or may be placed in another place.

That is, the cuff type manometer 26 may be placed at any place outside a vehicle where:
 the cuff type manometer 26 can be placed;
 a computer network can be used; and
 individuals can be identified.

The cuff type manometer 26 may be provided in a vehicle. In a case where a blood pressure of a seated person is measured by the cuff type manometer 26 in a vehicle, the blood pressure is basically measured while the vehicle is stopped. However, in a case where the vehicle travels while switching between automatic driving and manual driving, a blood pressure may be measured during automatic driving.

A method of acquiring a blood pressure of a seated person, i.e., biological information, using the cuff type manometer 26 and the biological sensors 10, 11 will be described.

As shown in FIG. 18, first, a person (seated person) measures a blood pressure with the cuff type manometer 26 outside the vehicle, in the embodiment, at home (Step S11). Thereby, blood pressure measurement value data, which is the first measurement value, is derived.

The communicator of the cuff type manometer 26 transmits the blood pressure measurement value data to the server 6 via the Internet (Step S12).

The control device 5 provided in the vehicle downloads the blood pressure measurement value data from the server 6 via the Internet (Step S13).

Time for the control device 5 to download the blood pressure measurement value data may be:
 time right after the communicator of the cuff type manometer 26 transmits the blood pressure measurement value data to the server;
 time when a person sits on the seat 1; or
 time for the biological sensors 10, 11 to estimate a blood pressure after a person sits.

A blood pressure of a seated person is estimated in a known blood pressure estimation method based on pulse wave transit time with the biological sensors 10, 11 provided in the seat 1 (Step S14). Thereby, the blood pressure estimation value data (pulse wave transit time), which is the second measurement value, is derived.

After the blood pressure estimation value data is derived, the control device 5 calibrates the blood pressure estimation value data with reference to the downloaded blood pressure measurement value data. The control device 5 calculates result of blood pressure measurement (Step S15). Thus, a "current" blood pressure of a person sitting on the seat 1 is derived more accurately based on the blood pressure measurement value data.

In the embodiment, the control device 5 calibrates the blood pressure estimation value data estimated in the blood pressure estimation method based on pulse wave transit time using the blood pressure measurement value data measured by the cuff type manometer 26. An expression for the calibration is as follows.

$$BP = \alpha \times PWTT + \beta \qquad \text{Expression 5}$$

BP is a blood pressure to be derived, and the unit is "mmHg". PWTT is a pulse wave transit time, and the unit is "sec". i.e., "second".

Letters "α" and "β" are parameters for a person. The blood pressure measurement value data is measured by the cuff type manometer 26 which is the first measurer. Values based on the blood pressure measurement data is applied to α and β. Explanation will be given with reference to FIGS. 16A to 16B. The blood pressure measurement value data is acquired by measuring a blood pressure of a person several times with the cuff type manometer 26. The letter "α" is an approximate straight line (i.e., a slope) derived from the blood pressure measurement value data. The letter "β" is a measurement value of blood pressure, that is, an intercept. Therefore, in FIG. 5, α is "−705" and β is "+235" for "Mr. A". For "Mr. B", α is "−670" and (is "+245". For "Mr. C", α is "−472" and β is "+188".

For example, "Mr. A" is a seated person. After Mr. A sits on the seat 1 of the vehicle, the pulse wave transit time "PWTT" is derived by the biological sensors 10, 11. By applying them to the above expression, a calibrated blood pressure value is calculated. For example, in a case where the pulse wave transit time "PWTT" derived by the biological sensors 10, 11 is 0.160 sec, a blood pressure is calculated as 122.2 mmHg.

Thus, a blood pressure of a seated person is acquired.

According to this Example, the cuff type manometer 26 not provided in the vehicle does not receive vibration from the vehicle. Therefore, the blood pressure estimation value data related to biological information of a person on board is calibrated with reference to the blood pressure measurement value data not affected by vehicle vibration. As a result, detection of accurate biological information is facilitated.

Even in a case where both the cuff type manometer 26 and the biological sensors 10, 11 are installed in a vehicle, the blood pressure estimation value data is calibrated with reference to the blood pressure measurement value data. Detection of more accurate biological information is facilitated as compared with a case where, for example, biological information of a person is acquired using only one of the cuff type manometer 26 and the biological sensors 10, 11. Acquiring such accurate biological information improves accuracy of the biological information and the scary/surprising accident information used in the above-described embodiment.

Example 5

In this Example, as shown in FIG. 19, a calibrator is provided in the information terminal S. The information terminal S performs short range wireless communication with the cuff type manometer 26, which is the first measurer, and the biological sensors 10, 11 (including the control device 5), which are the second measurers.

The information terminal S is a portable information processing device such as a mobile phone or a tablet terminal. The information terminal S includes a communicator for short-range wireless communication such as Bluetooth (registered trademark). In Example 2, the information terminal S is a mobile phone.

A calibration program that makes the information terminal S function as a calibrator is stored in memory included in the information terminal S. A controller included in the information terminal S executes the calibration program.

A person to be measured by the cuff type manometer 26 and the biological sensors 10, 11 uses the information terminal S.

The cuff type manometer 26 includes a short-distance wireless communicator to transmit the blood pressure measurement value data, which is the first measurement value, to the information terminal S.

The second measurer in this Example is constituted by the biological sensors 10, 11 and the control device 5. Thus, the control device 5 is communicably connected to the biological sensors 10, 11, and includes the short-range wireless communicator.

A method of acquiring a blood pressure (i.e., biological information) of a seated person using the cuff type manometer 26 and the biological sensors 10, 11 will be described.

As shown in FIG. 20, first, a person (seated person) measures a blood pressure with the cuff type manometer 26 outside a vehicle, in the example, at home (Step S21). Thereby, the blood pressure measurement value data, which is the first measurement value, is derived.

The blood pressure estimation value data is transmitted from the cuff type manometer 26 to the information terminal S using short-range wireless communication. In other words, the information terminal S receives the blood pressure measurement value data from the cuff type manometer 26 (Step S22).

A blood pressure of a seated person is estimated in a known blood pressure estimation method based on pulse wave transit time using the biological sensors 10, 11 provided in the seat 1 (Step S23). Thereby, the blood pressure estimation value data (pulse wave transit time), which is the second measurement value, is derived.

The control device 5 provided in the seat 1 transmits the blood pressure estimation value data to the information terminal S using short-range wireless communication. In other words, the information terminal S receives the blood pressure estimation value data from the control device 5 (Step S24).

The information terminal S calibrates the blood pressure estimation value data with reference to the blood pressure measurement value data, and calculates result of blood pressure measurement (Step S25). Thus, a "current" blood pressure of a person sitting on the seat 1 is derived more accurately based on the blood pressure measurement value data.

Time for the information terminal S to calibrate the blood pressure estimation value data may be:
  time right after the information terminal S receives the blood pressure estimation value data from the control device 5; or
  any time when a person (seated person) to be measured operates a touch panel of the information terminal S.

Thus, a blood pressure of a seated person is acquired.

According to this Example, the calibrator is provided in the information terminal S. The information terminal S performs short range wireless communication with the cuff type manometer 26, which is the first measurer, and the biological sensors 10, 11 (including the control device 5), which are the second measurers. The blood pressure measurement value data, which is the first measurement value data, is transmitted to the information terminal S in advance by short-range wireless communication. The blood pressure estimation value data is calibrated with reference to the blood pressure measurement value data even while the vehicle is running, for example, at a place far away from the cuff type manometer 26. Accurate biological information is acquired.

Example 6

In this Example, as shown in FIG. 21, a calibrator is provided in the information terminal S. The information terminal S performs short range wireless communication with the biological sensors 10, 11 (including the control device 5), which are the second measurers.

The blood pressure measurement value data acquired by the cuff type manometer 26, which is the first measurer, is transmitted to the information terminal S through the computer network N such as the Internet. The blood pressure estimation value data acquired by the biological sensors 10, 11 is transmitted to the information terminal S by short-range wireless communication.

The information terminal S includes a communicator for enabling connection to the computer network N such as the Internet. The information terminal S connects to the server 6 via the Internet. The information terminal S includes a communicator for short-range wireless communication such as Bluetooth (registered trademark).

The cuff type manometer 26 includes a communicator (not shown). The communicator uses the computer network N such as the Internet to transmit the blood pressure measurement value data to the outside. The cuff type manometer 26 connects to the server 6 via the Internet. The control device 5 communicably connected to the biological sensors 10, 11 includes a short-range wireless communicator.

A method of acquiring a blood pressure (i.e., biological information) of a seated person using the cuff type manometer 26 and the biological sensors 10, 11 will be described.

As shown in FIG. 22, first, a person (seated person) measures a blood pressure with the cuff type manometer 26 outside a vehicle, in the example, at home (Step S31). Thereby, the blood pressure measurement value data, which is the first measurement value, is derived.

The communicator of the cuff type manometer 26 transmits the blood pressure measurement value data to the server 6 via the Internet (Step S32).

The information terminal S downloads the blood pressure measurement value data from the server via the Internet N (Step S33).

Time for the information terminal S to download the blood pressure measurement value data may be:
time right after the communicator of the cuff type manometer 26 transmits the blood pressure measurement value data to the server;
time when a person sits on the seat 1; or
time for the biological sensors 10, 11 to estimate a blood pressure after a person sits.

A blood pressure of the seated person is estimated in a known blood pressure estimation method based on pulse wave transit time with the biological sensors 10, 11 provided in the seat 1 (Step S34). Thereby, the blood pressure estimation value data (pulse wave transit time), which is the second measurement value, is derived.

The control device 5 provided in the seat 1 transmits the blood pressure estimation value data to the information terminal S using short-range wireless communication. In other words, the information terminal S receives the blood pressure estimation value data from the control device 5 (Step S35).

The information terminal S calibrates the blood pressure estimation value data with reference to the blood pressure measurement value data, and calculates result of blood pressure measurement (Step S36). Thus, a "current" blood pressure of a person sitting on the seat 1 is derived more accurately based on the blood pressure measurement value data.

Time for the information terminal S to calibrate the blood pressure estimation value data may be:
time right after the information terminal S receives the blood pressure estimation value data from the control device 5; or
any time when a person (seated person) to be measured operates a touch panel of the information terminal S.

Thus, a blood pressure of a seated person is acquired.

According to this Example, the calibrator is provided in the information terminal S. The information terminal S performs short range wireless communication with a biological sensors 10, 11 (including the control device 5), which are the second measurers. The blood pressure measurement value data is transmitted to the calibrator provided in the information terminal S through the computer network N. The blood pressure measurement value data is the first measurement value data acquired by the cuff type manometer 26 which is the first measurer. The blood pressure estimation value data is calibrated with reference to the blood pressure measurement value data even while the vehicle is running, for example, at a place far away from the cuff type manometer 26. Accurate biological information is acquired.

INDUSTRIAL APPLICABILITY

The biological sensor and the vehicle seat according to the present invention facilitates accurate detection of biological information. It has high industrial applicability.

REFERENCE SIGNS LIST

First Embodiment

1 seat
2 seat cushion
3 seat back
4 headrest
5 control device
10 biological sensor
10A biological sensor
10B biological sensor
10C biological sensor
10D biological sensor
10E biological sensor
11 first sensor
11C first sensor
11E first sensor
12 second sensor
12D second sensor
12E second sensor
13 third sensor
14 first cushion material
14E cone
15 second cushion material Second Embodiment

1 seat
2 seat cushion
3 seat back
5 control device

C camera
10 biological sensor
11a biological sensor
11b biological sensor
11c biological sensor
12 transmitter of build detection sensor
13 receiver of build detection sensor
21 seat
22 seat cushion
23 seat back
24 headrest
25 lumbar support
31 seat
32 seat cushion
32a bank
32b ottoman
33 seat back
33a bank
33b shoulder support
34 headrest
35 air cell
36 air cell
37 air cell
38 air cell
39 air cell
41 seat
42 seat cushion
43 seat back
51 seat
52 seat cushion
53 seat back
54 headrest

Third Embodiment 1 seat
2 seat cushion
3 seat back
4 headrest
5 control device
N internet
S information terminal
10 biological sensor
11 biological sensor
26 manometer
26a display
27 cuff
27a air supply tube

Fourth Embodiment 1 seat
2 seat cushion
3 seat back
4 headrest
5 control device
6 server
7 database
8 learning unit (artificial intelligence)
9 vehicle
10 biological sensor
11 biological sensor
26 manometer
26a display
27 cuff
27a air supply tube

The invention claimed is:

1. A vehicle seat, comprising:
a seat body on which a person sits;
a biological sensor provided on a part of the seat body, the part being able to be moved to adjust a relative position with respect to a body of the seated person; and
a controller that controls movement of the part of the seat body,
wherein the biological sensor includes at least two sensors which detect vibration and which are layered, wherein, of the at least two sensors, one is a first sensor used to acquire biological information, and another is a second sensor used to remove noise,
wherein the controller presses the biological sensor against the seated person by operating the part, and
wherein, in a case where an output of the biological sensor pressed against the seated person exceeds a first threshold value, the controller makes the part move in a direction in which the biological sensor is separated from the seated person.

2. The vehicle seat according to claim 1, wherein the biological sensor further includes:
a first cushion material which is placed between the first sensor and the second sensor and which attenuates vibration,
wherein the first cushion material is layered with the first sensor and the second sensor.

3. The vehicle seat according to claim 2, wherein, in the biological sensor, the first cushion material is made of a urethane slab.

4. The vehicle seat according to claim 1, wherein the biological sensor further includes:
a third sensor which is used to remove noise,
wherein the third sensor is layered with the first sensor and the second sensor, and is on a side of the second sensor which does not face the first sensor.

5. The vehicle seat according to claim 2, wherein the biological sensor further includes:
a second cushion material that attenuates vibration,
wherein the second cushion material is layered with the first sensor, the second sensor, and the first cushion material, and is on a side of the second sensor which does not face the first sensor.

6. The vehicle seat according to claim 1, wherein, in the biological sensor, one of the first sensor and the second sensor is larger than another.

7. The vehicle seat according to claim 1, wherein, in a case where an output of the biological sensor moving away is below a second threshold value, the controller makes the part move in a direction in which the biological sensor approaches the seated person.

8. The vehicle seat according to claim 7, wherein, in a case where an output of the biological sensor approaching and contacting the seated person exceeds a third threshold value, the controller stops movement of the part.

9. The vehicle seat according to claim 1, wherein the seat body includes a build detection sensor which detects a build of the seated person and which sends build detection information to the controller.

10. The vehicle seat according to claim 9, wherein the build detection sensor includes:
a transmitter which is provided in the seat cushion and which irradiates the seat back with electromagnetic waves in a scanning line; and
a receiver which is provided in a grid pattern in the seat back and which receives the electromagnetic waves emitted from the transmitter.

* * * * *